(12) United States Patent
Casey et al.

(10) Patent No.: US 11,696,833 B2
(45) Date of Patent: Jul. 11, 2023

(54) SYSTEMS AND METHODS FOR ORTHOPEDIC IMPLANTS

(71) Applicant: Carlsmed, Inc., La Jolla, CA (US)

(72) Inventors: Niall Patrick Casey, Carlsbad, CA (US); Michael J. Cordonnier, Carlsbad, CA (US)

(73) Assignee: Carlsmed, Inc., Carlsbad, CA (US)

( * ) Notice: Subject to any disclaimer, the term of this patent is extended or adjusted under 35 U.S.C. 154(b) by 891 days.

(21) Appl. No.: 16/569,494

(22) Filed: Sep. 12, 2019

(65) Prior Publication Data

US 2020/0078180 A1 Mar. 12, 2020

Related U.S. Application Data

(60) Provisional application No. 62/730,336, filed on Sep. 12, 2018.

(51) Int. Cl.
| | |
|---|---|
| *A61F 2/30* | (2006.01) |
| *A61F 2/44* | (2006.01) |
| *B33Y 50/00* | (2015.01) |
| *B33Y 80/00* | (2015.01) |
| *G05B 19/4099* | (2006.01) |
| *A61B 34/10* | (2016.01) |

(52) U.S. Cl.
CPC .......... *A61F 2/30942* (2013.01); *A61B 34/10* (2016.02); *A61F 2/4455* (2013.01); *B33Y 50/00* (2014.12); *B33Y 80/00* (2014.12); *G05B 19/4099* (2013.01); *A61F 2002/3096* (2013.01); *A61F 2002/30943* (2013.01); *A61F 2002/30948* (2013.01); *A61F 2002/30952* (2013.01); *A61F 2002/30985* (2013.01); *G05B 2219/35134* (2013.01); *G05B 2219/49007* (2013.01)

(58) Field of Classification Search
CPC ... A61F 2/30942; A61F 2/4455; B33Y 50/00; B33Y 80/00
See application file for complete search history.

(56) References Cited

U.S. PATENT DOCUMENTS

| | | | |
|---|---|---|---|
| 4,704,686 | A | 11/1987 | Aldinger |
| 4,936,862 | A | 6/1990 | Walker et al. |

(Continued)

FOREIGN PATENT DOCUMENTS

| | | |
|---|---|---|
| CN | 104318009 A | 1/2015 |
| CN | 104353121 A | 2/2015 |

(Continued)

OTHER PUBLICATIONS

International Search Report and Written Opinion for International Patent Application No. PCT/US21/12065, dated Apr. 29, 2021 (19 pages).

(Continued)

*Primary Examiner* — Jason-Dennis N Stewart
(74) *Attorney, Agent, or Firm* — Perkins Coie LLP

(57) ABSTRACT

A system and computer-implemented method for manufacturing an orthopedic implant involves segmenting features in an image of anatomy. Anatomic elements can be isolated. Spatial relationships between the isolated anatomic elements can be manipulated. Negative space between anatomic elements is mapped before and/or after manipulating the spatial relationships. At least a portion of the negative space can be filled with a virtual implant. The virtual implant can be used to design and manufacture a physical implant.

30 Claims, 15 Drawing Sheets

(56) References Cited

U.S. PATENT DOCUMENTS

| | | |
|---|---|---|
| 5,431,562 A | 7/1995 | Andreiko et al. |
| D420,995 S | 2/2000 | Imamura |
| D436,580 S | 1/2001 | Navano |
| 6,315,553 B1 | 11/2001 | Sachdeva |
| 6,540,512 B1 | 4/2003 | Sachdeva |
| 6,696,073 B2 | 2/2004 | Boyce et al. |
| 6,772,026 B2 | 8/2004 | Bradbury |
| 6,932,842 B1 | 8/2005 | Litschko et al. |
| 6,978,188 B1 | 12/2005 | Christensen |
| 6,988,241 B1 | 1/2006 | Guttman |
| 7,174,282 B2 | 2/2007 | Hollister et al. |
| 7,187,790 B2 | 3/2007 | Sabol et al. |
| D548,242 S | 8/2007 | Viegers |
| D614,191 S | 4/2010 | Takano |
| 7,747,305 B2 | 6/2010 | Dean et al. |
| 7,756,314 B2 | 7/2010 | Karau et al. |
| 7,799,077 B2 | 9/2010 | Lang |
| D633,514 S | 3/2011 | Tokunaga |
| D656,153 S | 3/2012 | Imamura |
| 8,246,680 B2 | 8/2012 | Betz |
| 8,265,949 B2 | 9/2012 | Haddad |
| 8,275,594 B2 | 9/2012 | Lin |
| 8,337,507 B2 | 12/2012 | Lang |
| 8,394,142 B2 | 3/2013 | Bertagnoli |
| 8,457,930 B2 | 6/2013 | Shroeder |
| 8,532,806 B1 | 9/2013 | Masson |
| 8,556,983 B2 | 10/2013 | Bojarski et al. |
| 8,644,568 B1 | 2/2014 | Hoffman |
| 8,735,773 B2 | 5/2014 | Lang |
| 8,758,357 B2 | 6/2014 | Frey |
| 8,775,133 B2 | 7/2014 | Schroeder |
| 8,781,557 B2 | 7/2014 | Dean |
| 8,843,229 B2 | 9/2014 | Vanasse |
| 8,855,389 B1 | 10/2014 | Hoffman |
| 8,870,889 B2 | 10/2014 | Frey |
| 9,020,788 B2 | 4/2015 | Lang |
| D735,231 S | 7/2015 | Omiya |
| D737,309 S | 8/2015 | Kito |
| 9,198,678 B2 | 12/2015 | Frey et al. |
| 9,208,558 B2 | 12/2015 | Dean |
| D757,025 S | 5/2016 | Kim |
| D761,842 S | 7/2016 | Johnson |
| 9,411,939 B2 | 8/2016 | Furrer |
| 9,445,907 B2 | 9/2016 | Meridew |
| 9,452,050 B2 | 9/2016 | Miles et al. |
| D774,076 S | 12/2016 | Fuller |
| 9,542,525 B2 | 1/2017 | Arisoy et al. |
| 9,642,633 B2 | 5/2017 | Frey et al. |
| 9,693,831 B2 | 7/2017 | Mosnier et al. |
| 9,707,058 B2 | 7/2017 | Bassett |
| 9,715,563 B1 | 7/2017 | Schroeder |
| D797,760 S | 9/2017 | Tsujimura |
| D797,766 S | 9/2017 | Ibsies |
| D798,312 S | 9/2017 | Tsujimura |
| 9,757,245 B2 | 9/2017 | O'Neil et al. |
| D798,894 S | 10/2017 | Ibsies |
| 9,775,680 B2 | 10/2017 | Bojarski et al. |
| 9,782,228 B2 | 10/2017 | Mosnier et al. |
| D812,628 S | 3/2018 | Okado |
| 9,993,341 B2 | 6/2018 | Vanasse |
| 10,034,676 B2 | 7/2018 | Donner |
| D825,605 S | 8/2018 | Jann |
| D826,977 S | 8/2018 | Nakajima |
| 10,089,413 B2 | 10/2018 | Wirx-Speetjens et al. |
| D841,675 S | 2/2019 | Hoffman |
| 10,213,311 B2 | 2/2019 | Mafhouz |
| D845,973 S | 4/2019 | Jaycobs |
| D845,974 S | 4/2019 | Cooperman |
| D847,165 S | 4/2019 | Kolbenheyer |
| D848,468 S | 5/2019 | Ng |
| D849,029 S | 5/2019 | Cooperman |
| D849,773 S | 5/2019 | Jiang |
| 10,292,770 B2 | 5/2019 | Ryan |
| 10,299,863 B2 | 5/2019 | Grbic et al. |
| D854,560 S | 7/2019 | Field |
| D854,561 S | 7/2019 | Field |
| 10,390,958 B2 | 8/2019 | Maclennan |
| D860,237 S | 9/2019 | Li |
| D860,238 S | 9/2019 | Bhardwaj |
| D866,577 S | 11/2019 | Eisert |
| D867,379 S | 11/2019 | Ang |
| D867,389 S | 11/2019 | Jamison |
| 10,463,433 B2 | 11/2019 | Turner et al. |
| D870,762 S | 12/2019 | Mendoza |
| 10,512,546 B2 | 12/2019 | Kamer et al. |
| 10,517,681 B2 | 12/2019 | Roh et al. |
| D872,117 S | 1/2020 | Kobayashi |
| D872,756 S | 1/2020 | Howell |
| D874,490 S | 2/2020 | Dodsworth |
| D875,761 S | 2/2020 | Heffernan |
| D876,454 S | 2/2020 | Knowles |
| D876,462 S | 2/2020 | Li |
| D877,167 S | 3/2020 | Knowles |
| D879,112 S | 3/2020 | Hejazi |
| 10,588,589 B2 | 3/2020 | Bregman-Amitai et al. |
| 10,603,055 B2 | 3/2020 | Donner et al. |
| D880,513 S | 4/2020 | Wang |
| D881,908 S | 4/2020 | Sunil |
| D881,910 S | 4/2020 | Lin |
| 10,621,289 B2 | 4/2020 | Schroeder |
| 10,631,988 B2 | 4/2020 | Arnold et al. |
| D884,008 S | 5/2020 | Thornberg |
| 10,646,236 B2 | 5/2020 | Donner et al. |
| 10,646,258 B2 | 5/2020 | Donner et al. |
| 10,736,698 B2 | 8/2020 | Bohl |
| 10,751,188 B2 | 8/2020 | Guo et al. |
| D896,825 S | 9/2020 | Abel |
| D896,828 S | 9/2020 | Linares |
| D898,054 S | 10/2020 | Everhart |
| D899,438 S | 10/2020 | Crafts |
| 10,806,597 B2 | 10/2020 | Sournac et al. |
| 10,902,944 B1 | 1/2021 | Casey et al. |
| D916,868 S | 4/2021 | Evangeliou |
| D916,879 S | 4/2021 | Mitsumori |
| D918,253 S | 5/2021 | Choe |
| 11,000,334 B1 | 5/2021 | Young |
| D921,675 S | 6/2021 | Kmak |
| D921,677 S | 6/2021 | Kmak |
| D921,687 S | 6/2021 | Kmak |
| D924,909 S | 7/2021 | Nasu |
| D925,567 S | 7/2021 | Hayamizu |
| D927,528 S | 8/2021 | Heisler |
| D933,692 S | 10/2021 | Smith |
| D937,870 S | 12/2021 | Pinto |
| D937,876 S | 12/2021 | Harvey |
| D938,461 S | 12/2021 | Hoffman |
| D938,986 S | 12/2021 | Grossberg |
| D940,178 S | 1/2022 | Ang |
| D946,022 S | 3/2022 | Nuttbrown |
| D946,023 S | 3/2022 | Nuttbrown |
| D946,024 S | 3/2022 | Vogler-Ivashchanka |
| D946,616 S | 3/2022 | Tsai |
| D958,151 S | 7/2022 | Casey et al. |
| 2002/0007294 A1 | 1/2002 | Bradbury et al. |
| 2004/0104512 A1 | 6/2004 | Eidenschink |
| 2004/0171924 A1 | 9/2004 | Mire et al. |
| 2005/0049590 A1 | 3/2005 | Alleyne et al. |
| 2005/0271996 A1 | 12/2005 | Sporbert et al. |
| 2006/0009780 A1 | 1/2006 | Foley |
| 2007/0118243 A1 | 5/2007 | Schroeder |
| 2007/0276501 A1 | 11/2007 | Betz et al. |
| 2008/0161680 A1 | 7/2008 | von Jako |
| 2008/0195240 A1 | 8/2008 | Martin |
| 2008/0227047 A1 | 9/2008 | Lowe |
| 2009/0062739 A1 | 3/2009 | Anderson |
| 2010/0191088 A1 | 7/2010 | Anderson |
| 2010/0292963 A1 | 11/2010 | Schroeder |
| 2010/0324692 A1 | 12/2010 | Uthgenannt |
| 2011/0218545 A1 | 9/2011 | Catanzarite et al. |
| 2011/0301710 A1 | 12/2011 | Mather et al. |
| 2012/0010710 A1 | 1/2012 | Frigg |
| 2012/0084064 A1 | 4/2012 | Dzenis et al. |
| 2012/0116203 A1 | 5/2012 | Vancraen |
| 2012/0150243 A9 | 6/2012 | Crawford et al. |

(56) References Cited

U.S. PATENT DOCUMENTS

| | | |
|---|---|---|
| 2012/0191192 A1 | 7/2012 | Park |
| 2012/0287238 A1 | 11/2012 | Onishi |
| 2012/0296433 A1 | 11/2012 | Farin |
| 2012/0322018 A1 | 12/2012 | Lowe |
| 2013/0211531 A1 | 8/2013 | Steines et al. |
| 2013/0323669 A1 | 12/2013 | Lowe |
| 2014/0072608 A1 | 3/2014 | Karagkiozaki et al. |
| 2014/0074438 A1 | 3/2014 | Furrer |
| 2014/0081659 A1 | 3/2014 | Nawana et al. |
| 2014/0086780 A1 | 3/2014 | Miller |
| 2014/0100886 A1 | 4/2014 | Woods |
| 2014/0164022 A1 | 6/2014 | Reed et al. |
| 2014/0263674 A1 | 9/2014 | Cerveny |
| 2014/0350614 A1 | 11/2014 | Frey |
| 2015/0079533 A1 | 3/2015 | Lowe |
| 2015/0105891 A1 | 4/2015 | Golway et al. |
| 2015/0199488 A1 | 7/2015 | Falchuk |
| 2015/0213225 A1 | 7/2015 | Amarasingham |
| 2015/0324490 A1 | 11/2015 | Page |
| 2015/0328004 A1 | 11/2015 | Mafhouz |
| 2015/0332018 A1 | 11/2015 | Rosen |
| 2016/0001039 A1 | 1/2016 | Armour et al. |
| 2016/0015465 A1 | 1/2016 | Steines et al. |
| 2016/0030067 A1 | 2/2016 | Frey et al. |
| 2016/0074048 A1 | 3/2016 | Pavlovskaia et al. |
| 2016/0117817 A1 | 4/2016 | Seel |
| 2016/0143744 A1 | 5/2016 | Bojarski et al. |
| 2016/0184054 A1 | 6/2016 | Lowe |
| 2016/0210374 A1 | 7/2016 | Mosnier et al. |
| 2016/0217268 A1 | 7/2016 | Otto et al. |
| 2016/0242857 A1 | 8/2016 | Scholl |
| 2016/0300026 A1 | 10/2016 | Bogoni et al. |
| 2016/0354039 A1 | 12/2016 | Soto et al. |
| 2016/0378919 A1 | 12/2016 | McNutt et al. |
| 2017/0000566 A1 | 1/2017 | Gordon |
| 2017/0014169 A1 | 1/2017 | Dean et al. |
| 2017/0020679 A1 | 1/2017 | Maclennan |
| 2017/0035514 A1 | 2/2017 | Fox et al. |
| 2017/0061375 A1 | 3/2017 | Laster et al. |
| 2017/0068792 A1 | 3/2017 | Reiner |
| 2017/0135706 A1 | 5/2017 | Frey et al. |
| 2017/0143494 A1 | 5/2017 | Mahfouz |
| 2017/0143831 A1 | 5/2017 | Varanasi et al. |
| 2017/0216047 A1 | 8/2017 | Hawkes et al. |
| 2017/0220740 A1 | 8/2017 | D'Urso |
| 2017/0252107 A1 | 9/2017 | Turner et al. |
| 2017/0262595 A1 | 9/2017 | Vorhis |
| 2017/0340447 A1 | 11/2017 | Mahfouz |
| 2017/0354510 A1 | 12/2017 | O'Neil et al. |
| 2017/0367645 A1 | 12/2017 | Klinder |
| 2018/0008349 A1 | 1/2018 | Gillman |
| 2018/0113992 A1 | 4/2018 | Eltorai et al. |
| 2018/0116727 A1 | 5/2018 | Caldwell et al. |
| 2018/0168499 A1 | 6/2018 | Bergold et al. |
| 2018/0168731 A1 | 6/2018 | Reid et al. |
| 2018/0185075 A1 | 7/2018 | She |
| 2018/0233222 A1 | 8/2018 | Daley |
| 2018/0233225 A1 | 8/2018 | Experton et al. |
| 2018/0250075 A1 | 9/2018 | Cho |
| 2018/0303552 A1 | 10/2018 | Ryan |
| 2018/0303616 A1 | 10/2018 | Bhattacharyya et al. |
| 2018/0308569 A1 | 10/2018 | Luellen |
| 2018/0338841 A1 | 11/2018 | Miller et al. |
| 2019/0029757 A1 | 1/2019 | Roh et al. |
| 2019/0065685 A1 | 2/2019 | Pickover |
| 2019/0146458 A1 | 5/2019 | Roh et al. |
| 2019/0167435 A1 | 6/2019 | Cordonnier |
| 2019/0201106 A1 | 7/2019 | Siemionow |
| 2019/0262084 A1 | 8/2019 | Roh et al. |
| 2019/0266597 A1 | 8/2019 | Mohtar |
| 2019/0282367 A1 | 9/2019 | Casey et al. |
| 2019/0321193 A1 | 10/2019 | Casey et al. |
| 2019/0328929 A1 | 10/2019 | Kugler et al. |
| 2019/0333622 A1 | 10/2019 | Levin |
| 2019/0354693 A1 | 11/2019 | Yoon |
| 2019/0380792 A1 | 12/2019 | Poltaretskyi et al. |
| 2020/0021570 A1 | 1/2020 | Lin |
| 2020/0085509 A1 | 3/2020 | Roh et al. |
| 2020/0170802 A1 | 6/2020 | Casey et al. |
| 2020/0261156 A1 | 8/2020 | Schmidt |
| 2020/0289288 A1 | 9/2020 | Müller et al. |
| 2020/0315708 A1 | 10/2020 | Mosnier et al. |
| 2021/0059822 A1 | 3/2021 | Casey et al. |
| 2021/0064605 A1 | 3/2021 | Balint |
| 2021/0145519 A1 | 5/2021 | Mosnier et al. |
| 2021/0210189 A1 | 7/2021 | Casey et al. |
| 2021/0287770 A1 | 9/2021 | Anderson |
| 2021/0382457 A1 | 12/2021 | Roh et al. |
| 2022/0000556 A1 | 1/2022 | Casey et al. |
| 2022/0000625 A1 | 1/2022 | Cordonnier |
| 2022/0006642 A1 | 1/2022 | Maj et al. |
| 2022/0039965 A1 | 2/2022 | Casey et al. |
| 2022/0047402 A1 | 2/2022 | Casey et al. |
| 2022/0110686 A1 | 4/2022 | Roh et al. |
| 2022/0160405 A1 | 5/2022 | Casey et al. |
| 2022/0160518 A1 | 5/2022 | Casey et al. |

FOREIGN PATENT DOCUMENTS

| | | |
|---|---|---|
| CN | 204468348 U | 7/2015 |
| CN | 105796214 A | 7/2016 |
| CN | 106202861 A | 12/2016 |
| CN | 107220933 A | 9/2017 |
| CN | 113643790 A | 11/2017 |
| CN | 108670506 A | 10/2018 |
| CN | 110575289 A | 12/2019 |
| CN | 111281613 A | 6/2020 |
| CN | 112155792 A | 1/2021 |
| EP | 3120796 A1 | 1/2017 |
| WO | 9507509 A1 | 3/1995 |
| WO | 2004110309 A2 | 12/2004 |
| WO | 2010151564 A1 | 12/2010 |
| WO | 2012154534 A1 | 11/2012 |
| WO | 2014180972 A2 | 11/2014 |
| WO | 2016172694 A1 | 10/2016 |
| WO | 2019112917 A1 | 6/2019 |
| WO | 2019148154 A1 | 8/2019 |
| WO | 2022045956 A1 | 3/2022 |

OTHER PUBLICATIONS

U.S. Appl. No. 15/958,409 for Ryan, filed Apr. 21, 2017.

Endo, Kenji et al. "Measurement of whole spine sagittal alignment using the SLOT radiography of the SONIALVISION satire series clinical application." Medical Now, No. 78; Aug. 2015, 4 pages.

International Searching Authority, International Search Report and Written Opinion, PCT Patent Application PCT/US2018/063530, dated Feb. 12, 2019, 16 pages.

Materialise Mimics, "Efficiently turn scans into accurate virtual 3D models," <www.materialize.com/en/medical/software/mimics>, 1 page.

Pimenta, Dr. Luiz, "Current Surgical Strategies to Restore Proper Sagittal Alignment," Journal of Spine 2015, vol. 4. Issue 4, 2 pages.

Extended European Search Report for European Application No. 18885367.5, dated Aug. 16, 2021, 8 pages.

International Search Report and Written Opinion for International Application No. PCT/US21/44878, dated Nov. 16, 2021, 18 pages.

International Search Report and Written Opinion for International Application No. PCT/US21/45503, dated Jan. 11, 2022, 19 pages.

International Search Report and Written Opinion for International Patent Application No. PCT/US21/59837, dated Feb. 7, 2022, 19 pages.

Majdouline et al., "Preoperative assessment and evaluation of instrumentation strategies for the treatment of adolescent idiopathic scoliosis: computer simulation and optimization." Scoliosis 7, 21 (2012), pp. 1-8.

Eshkalak, S.K. et al., "The role of three-dimensional printing in healthcare and medicine." Materials and Design 194, Jul. 10, 20202, 15 pages.

Extended European Search Report for European Application No. 19859930.0, dated Jun. 22, 2022, 7 pages.

(56) References Cited

OTHER PUBLICATIONS

International Search Report and Written Opinion for International Patent Application No. PCT/US21/60074, dated Mar. 17, 2022, 21 pages.
Pruthi, G. et al., "Comprehensive review of guidelines to practice prosthodontic and implant procedures during COVID-19 pandemic." Journal of Oral Biology and Craniofacial Research 10, Oct. 17, 2020, 8 pages.
U.S. Appl. No. 17/463,054 for Casey et al., filed Aug. 31, 2021.
U.S. Appl. No. 17/518,524 for Cordonnier, filed Nov. 3, 2021.
U.S. Appl. No. 17/678,874 for Cordonnier, filed Feb. 23, 2022.
U.S. Appl. No. 17/702,591 for Roh et al., filed Mar. 23, 2022.
U.S. Appl. No. 17/835,777 for Cordonnier, filed Jun. 8, 2022.
U.S. Appl. No. 17/838,727 for Casey et al., filed Jun. 13, 2022.
U.S. Appl. No. 17/842,242 for Cordonnier, filed Jun. 16, 2022.
U.S. Appl. No. 17/851,487 for Cordonnier, filed Jun. 28, 2022.
U.S. Appl. No. 17/856,625 for Cordonnier, filed Jul. 1, 2022.
U.S. Appl. No. 17/867,621 for Cordonnier, filed Jul. 18, 2022.
U.S. Appl. No. 17/875,699 for Casey et al., filed Jul. 28, 2022.
U.S. Appl. No. 17/878,633 for Cordonnier, filed Aug. 1, 022.
U.S. Appl. No. 17/880,277 for Casey et al., filed Aug. 3, 2022.
International Search Report and Written Opinion received for counterpart International Application No. PCT/US2019/050885; dated Jan. 28, 2020 (17 pages).
International Search Report and Written Opinion received for International Application No. PCT/US2019/063855; dated Feb. 14, 2020 (15 pages).

| Surgeon: | Dr. X | | | |
|---|---|---|---|---|
| Patient ID: | 2018XXXXX | | | |
| Prescription ID: | 2018XXXXX | | | |
| Implant PNs: | 2018XXXXX<br>2018XXXXX<br>2018XXXXX<br>2018XXXXX | | | |
| Surgery date: | 10/12/2018 | | | |

| Metric | Pathology | Plan | | Modifications to Plan |
|---|---|---|---|---|
| Levels | L1 – S1 | L1 – S1 | | |
| PI | 55 deg | 55 deg | | n.a. |
| Lordosis (degrees)<br>- L1/2<br>- L2/3<br>- L3/4<br>- L4/5<br>- L5/S1 | 40 deg<br>5<br>5<br>7<br>8<br>15 | 60 deg<br>8<br>10<br>10<br>12<br>20 | | |
| Disc height<br>- L1/2<br>- L2/3<br>- L3/4<br>- L4/5<br>- L5/S1 | 45mm<br>7<br>9<br>10<br>11<br>8 | 57mm<br>9<br>12<br>14<br>12<br>10 | | |
| Coronal angle<br>- L1/2<br>- L2/3<br>- L3/4<br>- L4/5<br>- L5/S1 | 9 deg<br>2<br>10<br>0<br>-3<br>0 | 0<br>0<br>0<br>0<br>0<br>0 | | |
| Assessment | yellow | green | | Approval: XXX |

*FIG. 9*

SYSTEMS AND METHODS FOR ORTHOPEDIC IMPLANTS

CROSS-REFERENCE TO RELATED APPLICATION

This application claims priority to and the benefit of U.S. Provisional Patent Application No. 62/730,336, filed Sep. 12, 2018, which is hereby incorporated by reference in its entirety.

FIELD OF THE INVENTION

The field of the invention generally relates to orthopedic implants, including spinal implants, and methods for designing and producing them.

BACKGROUND

Orthopedic implants are used to correct a variety of different maladies. Orthopedic surgery utilizing orthopedic implants may include one of a number of specialties, including: spine surgery, hand surgery, shoulder and elbow surgery, total joint reconstruction (arthroplasty), skull reconstruction, pediatric orthopedics, foot and ankle surgery, musculoskeletal oncology, surgical sports medicine, and orthopedic trauma. Spine surgery may encompass one or more of the cervical, thoracic, lumbar spine, or the sacrum, and may treat a deformity or degeneration of the spine, or related back pain, leg pain, or other body pain. Irregular spinal curvature may include scoliosis, lordosis, or kyphosis (hyper- or hypo-), and irregular spinal displacement may include spondylolisthesis. Other spinal disorders include osteoarthritis, lumbar degenerative disc disease or cervical degenerative disc disease, lumbar spinal stenosis or cervical spinal stenosis.

Spinal fusion surgery may be performed to set and hold purposeful changes imparted on the spine during surgery. Spinal fusion procedures include PLIF (posterior lumbar interbody fusion), ALIF (anterior lumbar interbody fusion), TLIF (transverse or transforaminal lumbar interbody fusion), or LLIF (lateral lumbar interbody fusion), including DLIF (direct lateral lumbar interbody fusion) or XLIF (extreme lateral lumbar interbody fusion).

The goal of interbody fusion is to grow bone between vertebra in order to seize the spatial relationships in a position that provides enough room for neural elements, including exiting nerve roots. An interbody implant device (or interbody implant, interbody cage, or fusion cage, or spine cage) is a prosthesis used in spinal fusion procedures to maintain relative position of vertebra and establish appropriate foraminal height and decompression of exiting nerves. Each patient may have individual or unique disease characteristics, but most implant solutions include implants (e.g. interbody implants) having standard sizes or shapes (stock implants).

BRIEF DESCRIPTION OF THE DRAWINGS

FIG. 9 shows a representation of a surgical planning user interface.

DETAILED DESCRIPTION

Figure 1:
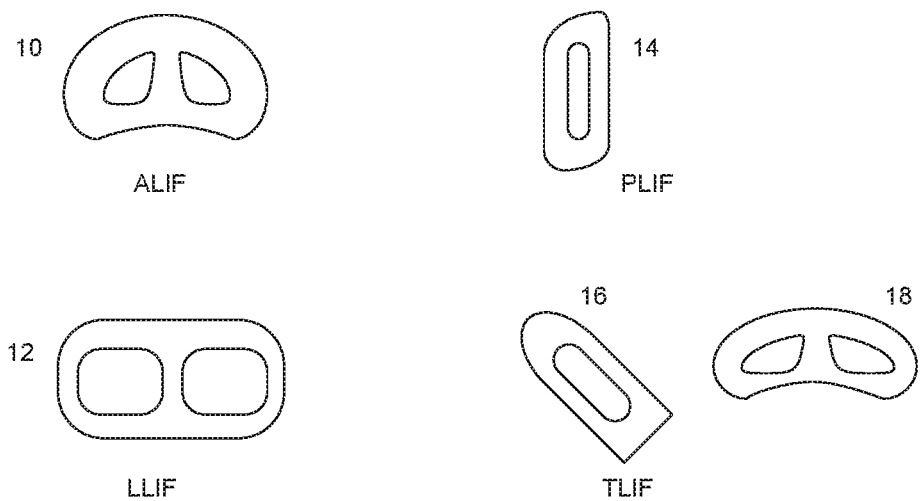
FIG. 1 shows a variety of traditional interbody implants.

A patient-specific medical device and an efficient method of producing a patient-specific interbody implant is described in the embodiments herein. Devices according to embodiments described herein may include interbody implants, fusion cages, or other implants. The interbody implants are typically intended to be placed in the space (created by surgical intervention) between two vertebrae. In fusion surgeries, the intervertebral disc may be surgically removed prior to the placement of the interbody implant. The lower (inferior) side of an interbody implant is intended to abut at least a portion of an upper (superior) side of a first vertebrae and the superior endplate of the interbody implant is intended to abut at least a portion of an inferior endplate of a second vertebrae.

Insufficient contact and load transfer between the vertebrae (anatomy) and the interbody implant (device) can produce inadequate fixation. Inadequate fixation can allow the cage to move relative to the vertebrae. Furthermore, insufficient contact area or fixation between the interbody implant and the vertebrae can result in micro- and/or macro-motions that can reduce the opportunity for bone growth and fusion to occur. If enough motion occurs, expulsion of the interbody implant or subsidence of the interbody implant into the adjacent vertebrae can result.

Traditional implants are selected intraoperatively from a surgical kit containing likely sizes and shapes depending on the surgical approach and patient anatomy. Selection of implant size is performed by the surgeon during the surgery while the patient's spine is exposed. Often, minimal consideration is paid to implant size prior to the surgery. The method for selecting implant size is "trialing," whereby the surgeon uses a series of incrementally sized implant proxies to determine the appropriate implant size and shape. This method presents several opportunities for improvements.

Significant intra-operative attention is paid to the posterior height and sagittal angle of the interbody implants; however, minimal attention is paid to the lateral heights and coronal angle of the interbody implants. Even with the attention paid to the sagittal height, the implants available in surgery only come in stock sizes that are unlikely to provide optimal solutions for the particular patient or particular interbody space. Additionally, traditional stock implants do not provide any options for variable coronal angles. By selecting stock implants intraoperatively from a fixed assortment of implant sizes, the surgeon is unable to provide to the patient an optimal solution for correction of the particular spinal deformity or pathological malalignment causing patient pain.

Furthermore, intraoperative selection of stock implants requires shipment and delivery of sufficient implants to cover the wide variety of patients and their unique interbody spaces. The shipping, sterilization, processing, and delivery of enough implants to surgery can be characterized as logistically burdensome and expensive. It is not uncommon for more than fifty implants to be delivered to a surgery that requires only one implant.

In one typical fusion procedure, posterior fixation devices (pedicle screws, spinal rods) are used to stabilize the spine. Additionally, anterior interbody implants provide spacing and decompression of neural elements and a location for interbody fusion (bone growth between two vertebra).

Improper or sub-optimal sizing of interbody implants can result in implant failures. If the interbody space is not sufficiently filled, posterior implants (including rods and plates) are required to carry more dynamic loads prior to fusion. The typical failure mode of spinal rods include fracture due to dynamic loads; the increased magnitude of the movement due to an undersized interbody implant only exacerbates the condition, leading to more implant failures.

Patient-specific interbody implants can be designed for optimal fit in the negative space created by removal of the disc and adjustment of the relative position of vertebrae. Surgical planning software can be used to adjust the relative positions of vertebrae and define the negative space between the vertebrae. Modifying the spatial relationship between adjacent vertebrae within a virtual design space can provide a definition of the 3D negative space into which an interbody can be delivered. Software can further be used to compare the original pathology to the corrected positions of the vertebrae. The optimal size and shape of patient-specific implants can prevent or reduce instances of dynamic failure of posterior implants.

Presently, intraoperative imaging often requires radiation. Exposure to radiation should be reduced as low as reasonably possible. Surgeries using stock interbody implants require trialing to inform the selection of the stock implant. Patient-specific implants do not require trialing, as the size and shape of the implant has been determined prior to the surgery using preoperative imaging and planning software.

The imaging tools available to the surgeon during surgery typically only include mobile radiography (bedside x-ray, c-arm, o-arm). The use of mobile radiography exposes surgeons, staff, and patients to intraoperative radiation. The operating room environment does not provide the same radiation shielding capabilities that a standard dedicated radiology room provides (leaded walls, leaded glass, etc.). Because of the desire to reconcile radiographic images with visible (and invisible) anatomy, avoid sensitive anatomy, and understand relative anatomical positions, surgeons are often in close proximity to or within the field of radiation during intraoperative imaging. It is advantageous to reduce or eliminate radiation exposure to the participants of surgery.

One method of designing patient-specific interbody implants includes capturing important anatomical geometry and relative positioning using computed tomography (CT) or another imaging modality (MRI, simultaneous bi-planar radiography, etc.). The image data can be reconstructed into volumetric data containing voxels that are representative of anatomy. Following the scan, the collected data can be ported to a workstation with software to enable segmentation of relevant anatomy. A process called segmentation separates voxels representing bony anatomy from the other anatomy. Isolation of individual bony structures enables a user to appreciate each bony structure independently. Furthermore, following isolation, the relationships between individual vertebrae (distances, angles, constraints, etc.) can be manipulated. Together with a surgeon, an engineer can manipulate the vertebrae thereby changing the spacing between the virtual anatomical structures. Manipulations can include translations along an axis or curve, rotation about an axis or centroid, or rotation about the center of mass, among other movements. Consideration is to be paid to the virtual manipulations to ensure they are representative of anatomical constraints and manipulations that can be achieved in a surgical setting. After the virtual manipulations of select vertebrae, the newly created negative space between the vertebrae can be mapped and characterized using design software. One way of mapping the negative 3D space is to (1) select a bounding anatomical feature, such as a vertebral endplate, (2) create a best-fit plane through the surface, (3) define a perimeter of the anatomical feature, and (4) extrude a volume defined by the perimeter and perpendicular to the best-fit plane to the interface of another anatomical feature.

The newly created negative space between virtual vertebrae can be used to determine geometric parameters (dimensions, angles, heights, surfaces, topographies, footprints, etc.) and external envelope for optimal interbody implants.

After the external envelope for the patient-specific interbody (PSIB) implant has been determined, internal features, including lattice, struts, and apertures, can be designed. The internal features will determine the strength and bone incorporation qualities. Internal features can be engineered to provide favorable conditions for osteo-integration, bony on-growth, bony in-growth, and bony through-growth. Internal features can also be designed to resist or allow deformation, resulting in an optimal structural stiffness or compliance according to the physiological demands. In some patients, reducing the strength (stiffness) of the implant may create less instances of implant subsidence into the neighboring bones. In other patients, a stronger or stiffer implant may be designed to handle larger anticipated anatomical loads.

In some embodiments, a system and computer-implemented method for manufacturing an orthopedic implant involves segmenting features in an image of anatomy. The features can be anatomy of interest, such as bone, organs, etc. Anatomic elements (e.g., vertebrae, vertebral disks, etc.)

can be isolated. Spatial relationships between the isolated anatomic elements can be manipulated. Before and/or after manipulating the spatial relationships, a negative space between anatomic elements can be mapped. At least a portion of the negative space can be filled with a virtual implant. The virtual implant can be used to select, design, and/or manufacture a patient-specific implant.

FIG. 1 shows a variety of typical interbody implants. Each of the implants is surgically inserted using different anatomical approaches. ALIF (Anterior Lumbar Interbody Fusion) implant 10 is inserted from the anterior, through an incision in the abdomen. LLIF (Lateral Lumbar Interbody Fusion) implant 12 is inserted from a lateral direction, through an incision in the side. PLIF (Posterior Lumbar Interbody Fusion) implant 14 is inserted from a posterior direction, through an incision in the back. TLIF (Transforaminal Lumbar Interbody Fusion) implant 16 is also inserted from a posterior direction, through an incision in the back. The PLIF device is typically inserted parallel to the sagittal plane; whereas, the TLIF device is typically inserted through a neural foramen on a trajectory that is oblique to the sagittal plane.

Figure 2:
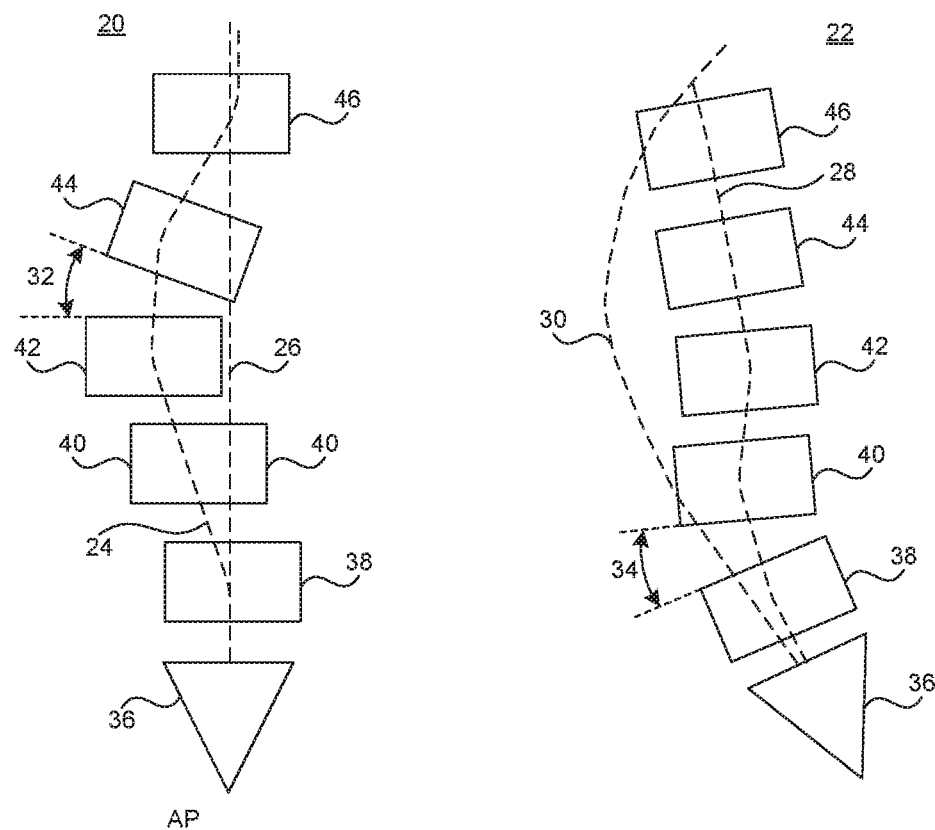
FIG. 2 shows a representation of a spine with a pathological deformity such as adult degenerative scoliosis.

FIG. 2 shows representations of a lumbar spine with adult degenerative scoliosis when viewed in the coronal plane 20 and sagittal plane 22. Sacrum 36 and lumbar vertebrae L5 38, L4 40, L3 42, L2 44, and L1 46 are shown in both coronal view 20 and sagittal view 22. Lumbar curvatures (coronal 24, sagittal 28) drawn through vertebrae centroids can be used to characterize the deformity of the spine. Additionally, angles between vertebrae 32, 34 can also be used to characterize deformities. Ideal coronal curvature 26 and sagittal curvature 30 can be superimposed on the Anterior-Posterior (AP) view 20 and Lateral (LAT) view 22.

Figure 3:
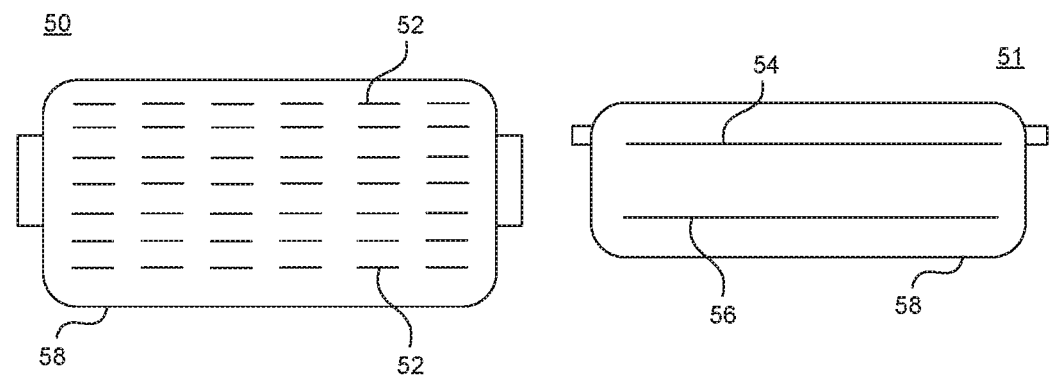
FIG. 3 shows a representation of a typical surgical implant kit containing stock implants delivered to spinal surgery.

FIG. 3 shows a representative stock interbody kit that is typically delivered to a single surgery. Top view 50 depicts a tray 54 containing the matrix of interbody implants 52. Side view 51 show trays 54, 56 that contain implants and instruments to be used in surgery. Each kit is contained within a steam sterilization case and trays 54, 56 that allow for steam to penetrate the case and sterilize the contents. The number of stock implants 52 contained within kit 50 can number over one-hundred. Instruments contained within kit 58 can be greater than twenty.

Figure 4:
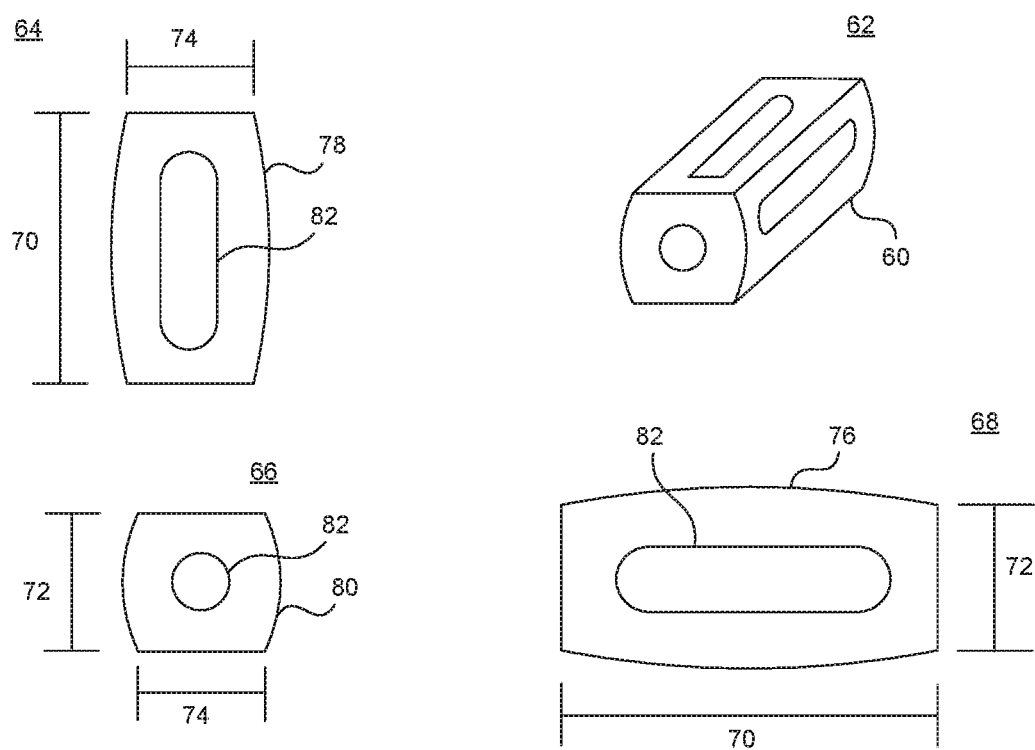
FIG. 4 shows a representation of a typical stock implant including several views.

FIG. 4 shows four views of a typical stock implant 60 (isometric 62, top 64, front 66, side 68 views). Length 70, width 74, and height 72 are fundamental dimensions that define the overall envelope for stock implants. Additionally, curvatures and radii 76, 78, 80 can further describe the implant geometry. Also depicted in stock implant 62 are apertures 82 that allow bone to grow from adjacent vertebral endplates through the implant for fusion thereby completing fusion of adjacent vertebrae.

Each stock implant has several dimensions that vary for a specific instance of an implant (length, width, height, curvatures, radii, etc.). Although these dimensions are infinitely variable, space, logistics and expense limit inclusion of all instances within a surgical kit 50.

Figure 5:
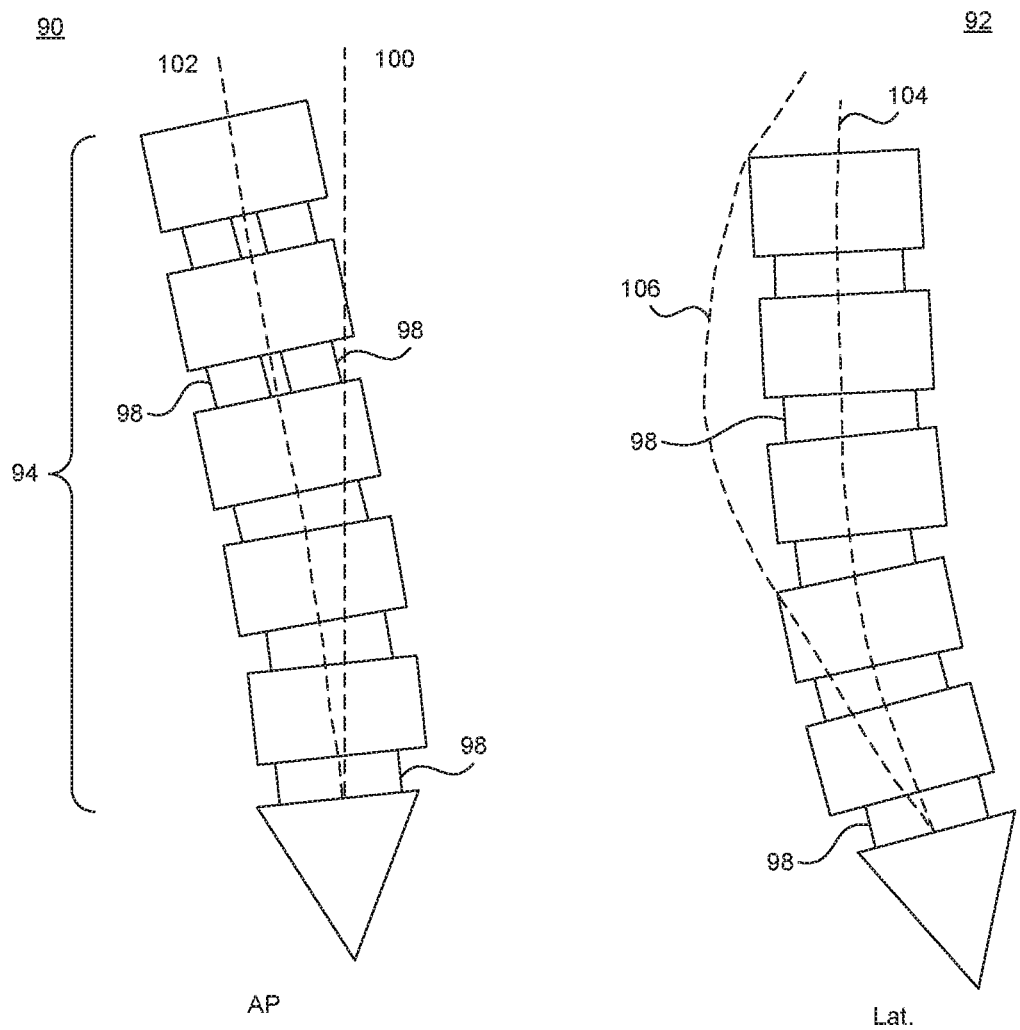
FIG. 5 shows a representation of a spine with a pathological deformity that has been surgically corrected with traditional stock interbodies.

FIG. 5 shows the spine from FIG. 2 as treated with stock interbody implants. Implants 98 are positioned between the vertebrae during surgery to correct the spinal deformity. Due to the inability to provide all possible variations of stock implants to each surgery, correction of a complex deformity is limited by the selection of implants from an existing matrix of instances. Since each deformity is unique to the patient, correction of the deformity using stock implants is necessarily suboptimal.

As seen in FIG. 5, suboptimal coronal and sagittal deformities can still exist following surgery. The post-surgical coronal curvature 100 deviates from the optimal coronal curvature 102. Additionally, the post-surgical sagittal curvature 104 deviates from the optimal sagittal curvature 106. Pathological curvatures and associated pain are the proximal reasons for undergoing surgery. If correction of the curvature is not achieved, the patient remains at risk for continued pain. One method of providing correction to pathological curvatures is to implant devices that, when incorporated into the spinal column, re-align the spine to the appropriate curvature and relieve patient symptoms. AP 90 and lateral view 92 depicts five interbody implants 98 that aim to correct the complex deformity, realign the spine, and/or relieve pain. If stock implants 98 are not properly sized and shaped, the curvature (and associated pain) may remain. Stock implants 98 cannot provide the optimal amount of correction due to the limited nature of the offering during surgery.

Figure 6:
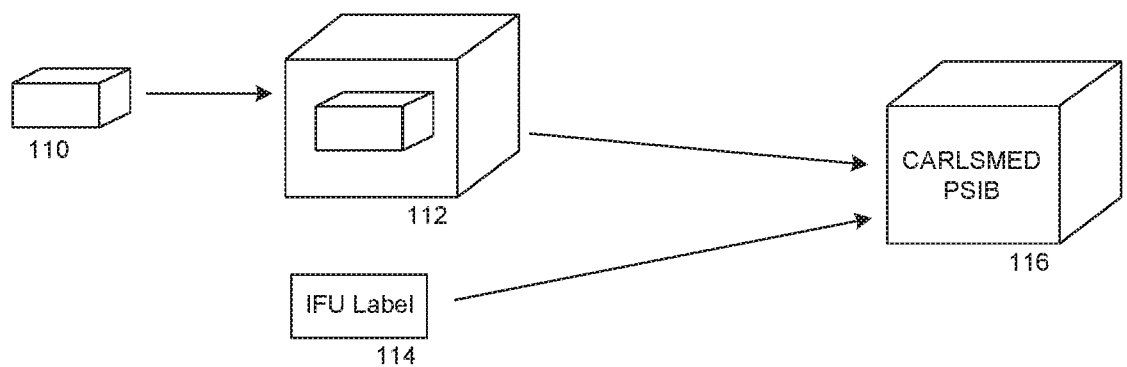
FIG. 6 shows isolated lumbar vertebrae and coordinate systems to guide adjustment of relative positions between vertebrae.

FIG. 6 shows a patient-specific interbody contained within packaging. In one embodiment implant 110 is inserted into one or many sterilization envelopes 112 that can be sterilized and opened during surgery. Label 114 and other required identifying documents can be included with the packaging or affixed to the sterilization envelopes 112 to identify implant 110. Identification can include patient identifier, surgeon identifier, geometric parameters, spinal level for insertion, method of insertion, and date of surgery among other pieces of data.

Figure 7:
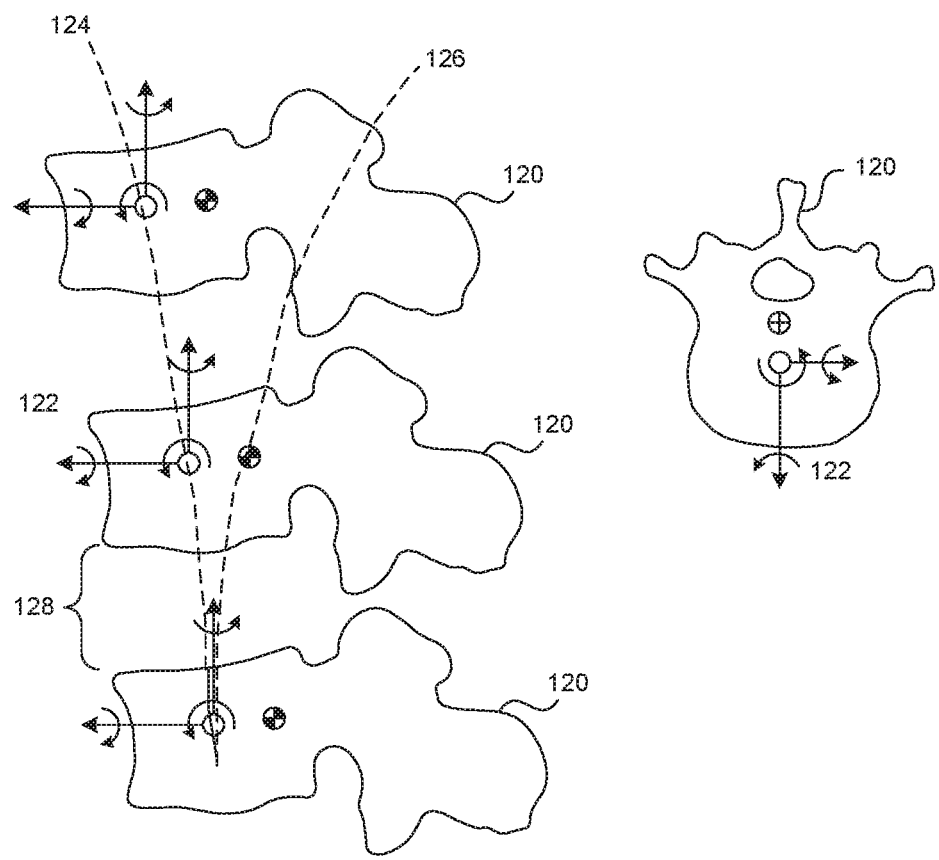
FIG. 7 shows a representation of a patient specific-implant and packaging as delivered to spinal surgery.

FIG. 7 shows lumbar vertebrae, coordinate frames, and lumbar curvatures. Vertebrae 120 is shown in relation to other lumbar vertebrae. The relationships between the vertebrae is often the cause of patient pain and subsequent surgical intervention. Often adult degenerative scoliosis or another pathology cause the vertebrae to exert pressure on neural elements, causing patient pain. Correction of positioning or re-aligning of the vertebrae can alleviate pain. The goal of the surgery is to re-align the vertebrae, remove pressure on the nerves, and fuse the vertebrae in place to provide lasting relief of pressure on the nerves.

Vertebrae 120 can be moved along coordinate systems 122 as defined by the user. Manipulations can occur as (1) translations along predetermined or user-defined axis, (2) rotations about predetermined or user-defined axis, (3) translations along predetermined or user-generated curves, and (4) rotations about predetermined or user-generated curves.

In one embodiment, coordinate systems 122 based on the centroid for each vertebra is displayed in order to facilitate manipulation of each vertebrae. In another embodiment, curvatures representing a best-fit curve between centroids of adjacent vertebrae is created. Another curve representing the optimal curvature of vertebrae can be used to manipulate vertebrae. A 'snap' feature can cause the vertebrae aligned in pathological conditions to automatically be positioned on a desired curve that represents optimal alignment for a patient.

In another embodiment, intersections between virtual solid models can be calculated. Where intersections or overlap of bony anatomy is detected by the planning software, they can be resolved by an engineer, technician, or physician. Anatomical constraints, such as facet joint mobility, angles of facet articulating surfaces, and articulating surface size, must be considered during the alignment of virtual vertebrae. By manipulating the virtual models of vertebrae, the negative three-dimensional space between the vertebrae can be appreciated. After correction of the virtual vertebrae has occurred, the negative space that results from the correction can be described. The description of the negative space can be used to inform the design of the interbody implant.

Figure 15:
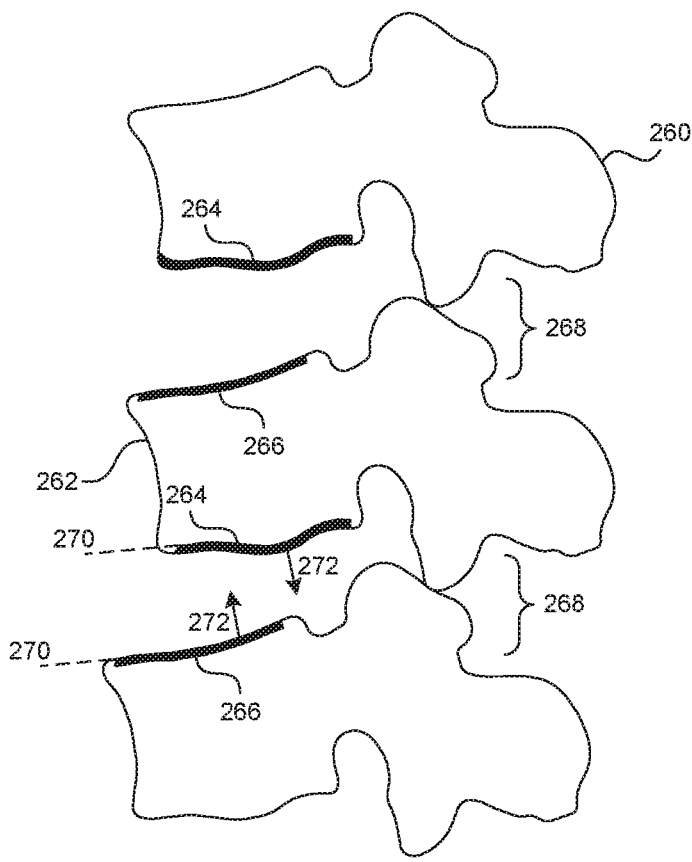
FIG. 15 shows three lumbar vertebrae and highlighted vertebral endplates.
Figure 16:
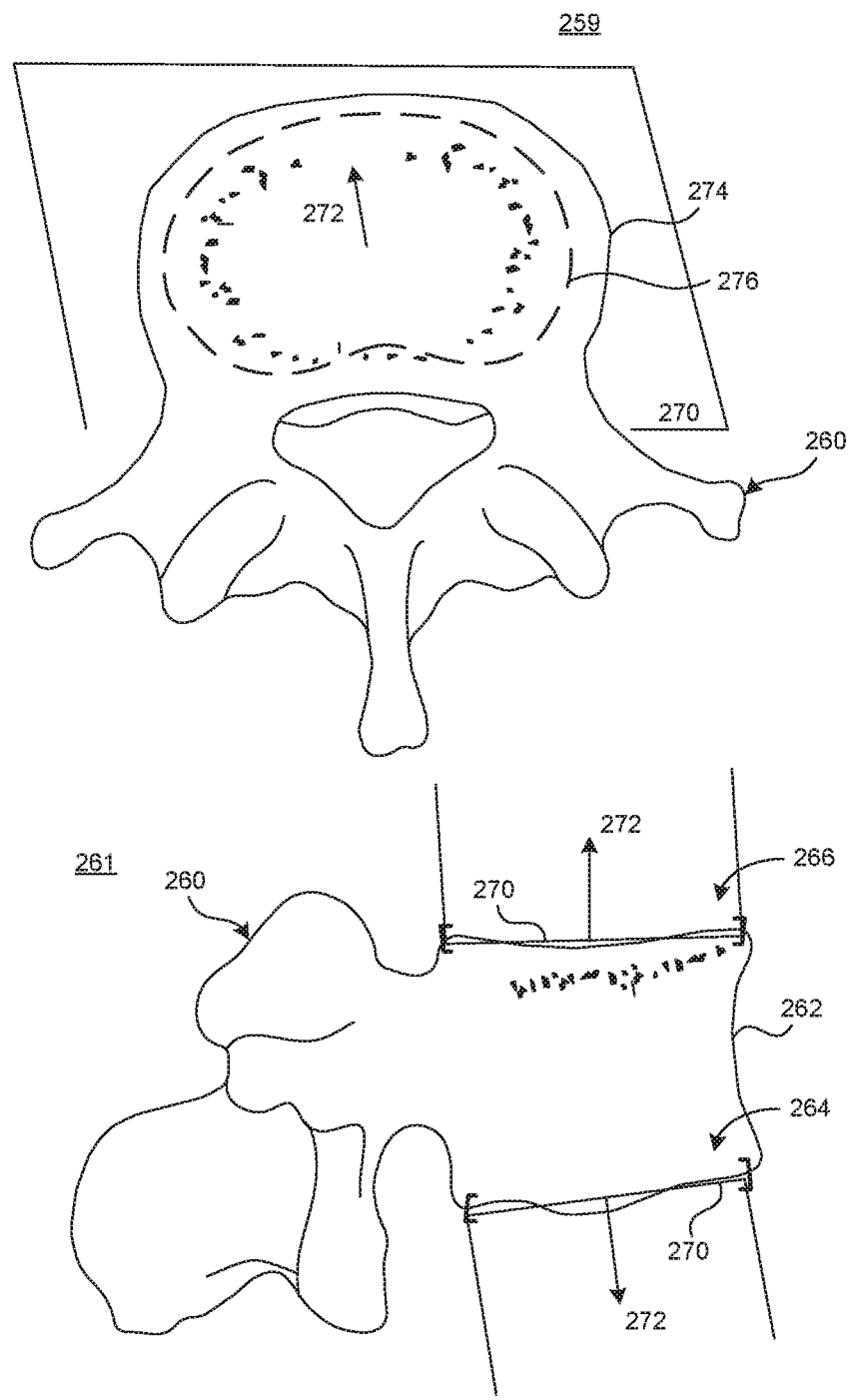
FIG. 16 shows top and side views of a vertebra.

FIG. 15 shows three lumbar vertebra and highlighted vertebral endplates. FIG. 16 shows an individual vertebra as shown in axial 259 and lateral 261 views. Vertebrae 260 have features including an anterior vertebral body 262 containing endplates. Emphasis has been added to endplates in order to appreciate the anatomical bounding features 264, 266 which can be used to define the negative 3D volume between vertebral bodies. Facet joint 268 restricts motion between vertebra. In order to appreciate the 3D volume between the vertebrae, a best-fit plane 270 can be passed through the anatomical bounding features 264, 266. Vector 272, perpendicular to best-fit plane 270, can be constructed to provide direction for extruding a volume. Perimeter 274 can be drawn on plane 270. Perimeter 274 can be extruded to opposing endplates 264, 266 or bounding anatomical features to define the negative 3D space. A portion of the negative 3D space 276 can be used to describe an implant 216.

In one embodiment, implant boundary 276 can be drawn on plane 270 to represent an external shape of implant 216. Boundary 274 can be projected from plane 270 to opposing anatomical endplates 264, 266 to define the 3D shape of implant 216.

Implant 216 can be manufactured using one or more additive manufacturing or subtractive (traditional) manufacturing methods. Additive manufacturing methods include, but are not limited to: three-dimensional printing, stereolithography (SLA), selective laser melting (SLM), powder bed printing (PP), selective laser sintering (SLS), selective heat sintering (SHM), fused deposition modeling (FDM), direct metal laser sintering (DMLS), laminated object manufacturing (LOM), thermoplastic printing, direct material deposition (DMD), digital light processing (DLP), inkjet photo resin machining, and electron beam melting (EBM). Subtractive (traditional) manufacturing methods include, but are not limited to: CNC machining, EDM (electrical discharge machining), grinding, laser cutting, water jet machining, and manual machining (milling, lathe/turning).

Figure 8:
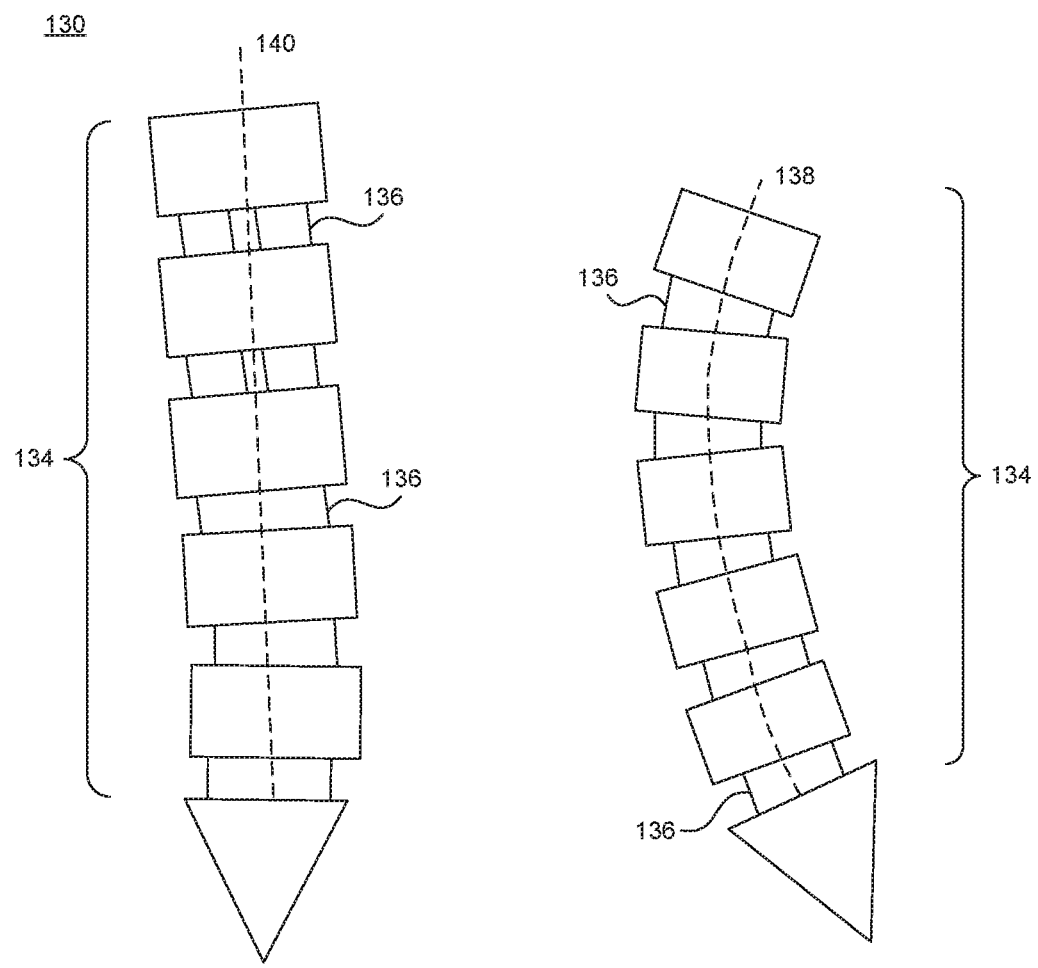
FIG. 8 shows a representation of a spine with a pathological deformity that has been surgically corrected with patient-specific interbodies.

FIG. 8 shows AP 130 and lateral 132 images of a lumbar spine that has been treated with patient-specific implants. The curves 138, 140 through the vertebrae of the lumbar spine 134 show that optimal alignment has occurred following placement of patient-specific interbodies 136. The manipulation of the virtual vertebrae has aligned the vertebrae. In this embodiment, the negative space between each vertebra can be optimally filled with virtual interbody implants. The parameters of the implants can be used to manufacture each interbody implant. Each implant can be manufactured using 3D printing. The implants can be packaged (including identifiers, labels, and instructions), sterilized, and delivered to surgery.

FIG. 9 shows a graphical display of a surgical planning software application. In one embodiment, software planning application 150 displays graphical and text information in several panes (152-166). In patient information pane 152, information about the patient, surgeon, and surgery can be displayed. Metric pane 154 can display parameters of interest to the user. Information like anatomical metric fields (pelvic incidence, lumbar lordosis, angle between vertebrae, distance between vertebrae, disc height, sagittal vertical axis, sacral slope, pelvic tilt, Cobb angle, etc.) can be selected and displayed.

Three columns containing six panes 156, 158, 160, 162, 164, 166 can be used to easily compare pathologic anatomy and corrected anatomy. In one embodiment, a column displaying information about the pathology with panes 156, 158 can show a virtual model of the spine 156 above the relative metrics of that spine 158. The displayed spine can be rotated (zoomed, panned, etc.) to better display areas of interest. Another column containing panes 160, 162 can display images and information (anatomic metrics) about the corrected spine and patient-specific implants in place.

The right column containing pane 164 can display images of pathological and corrected spine superimposed upon each other. The displayed spines can be rotated (zoomed, panned, etc.) to better display areas of interest. Pane 166 can display some important specifications of the patient-specific interbody implants, including posterior height, sagittal angle, coronal angle, anterior-posterior length, and width.

Figure 10:
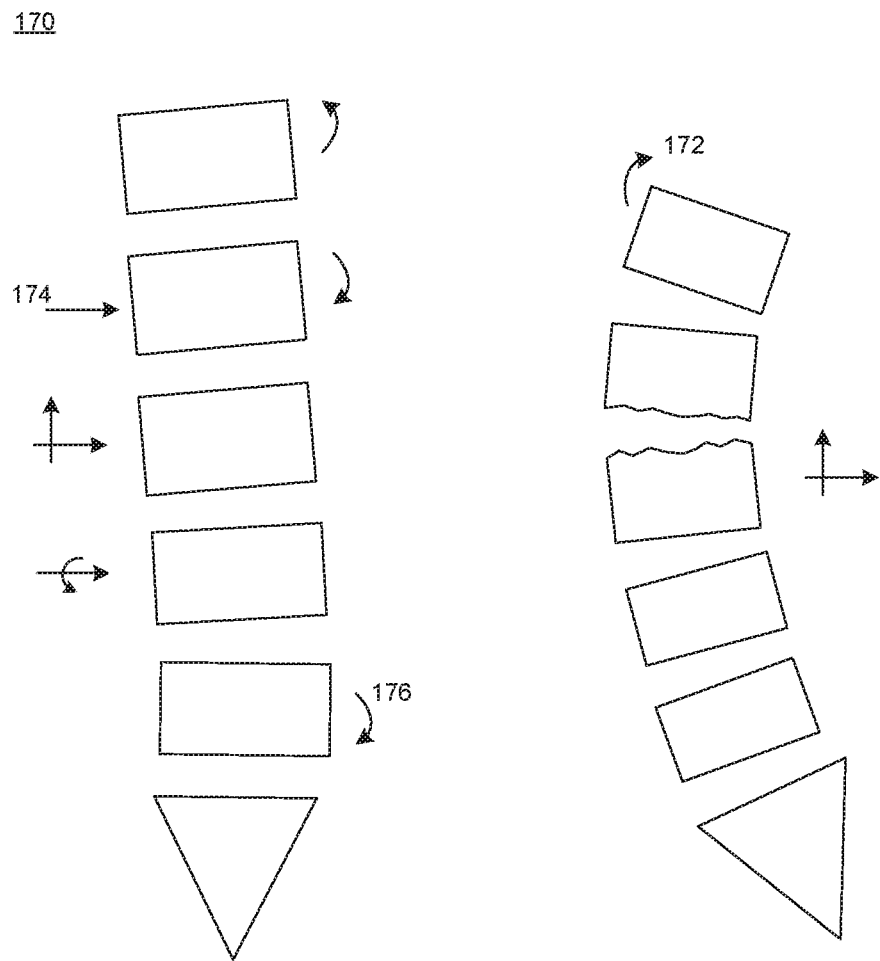
FIG. 10 shows a representation of a surgical planning user interface with tools to enable relative adjustments of vertebrae positioning.

FIG. 10 shows a lumbar spine 171 and graphical representations of the corrective maneuvers required to align the spine. AP 170 and lateral 172 images can be shown in order to provide the clinician with a better understanding of the correction that is required to reposition the spine in alignment. Arrows 174, 176 represent manipulations, maneuvers, rotations, or translations that will bring the spine back into alignment.

Figure 11:
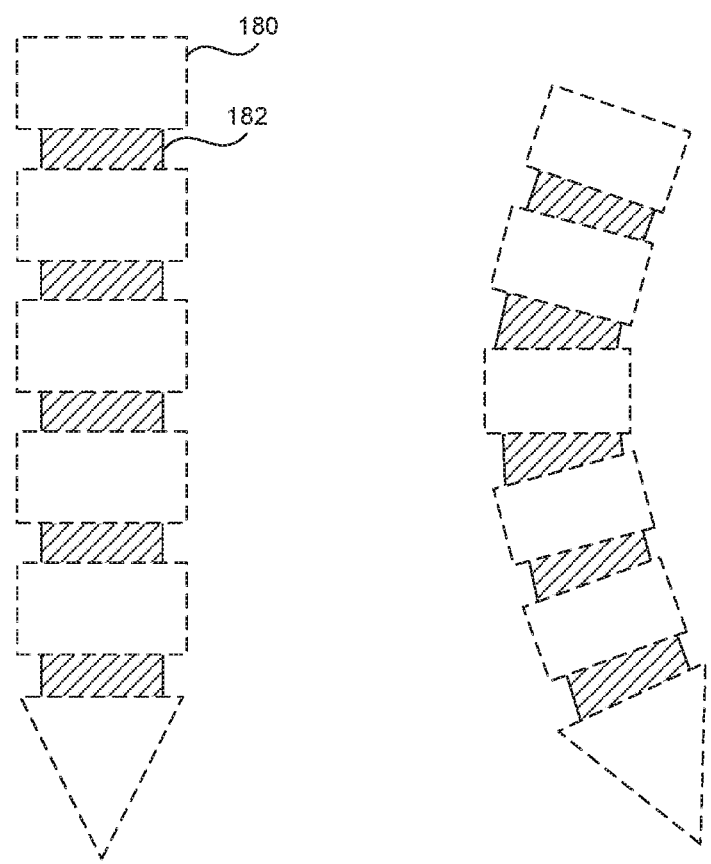
FIG. 11 shows a representation of a lumbar spine with the negative space between the vertebrae highlighted.

FIG. 11 shows the corrected spine with the patient-specific interbody implants in place. Each interbody implant 182 is highlighted while the corrected anatomy 180 is displayed as semi-transparent to allow for improved appreciation of the design of each implant. The images can be rotated, panned, or zoomed to provide better visibility to areas of interest.

Figure 12:
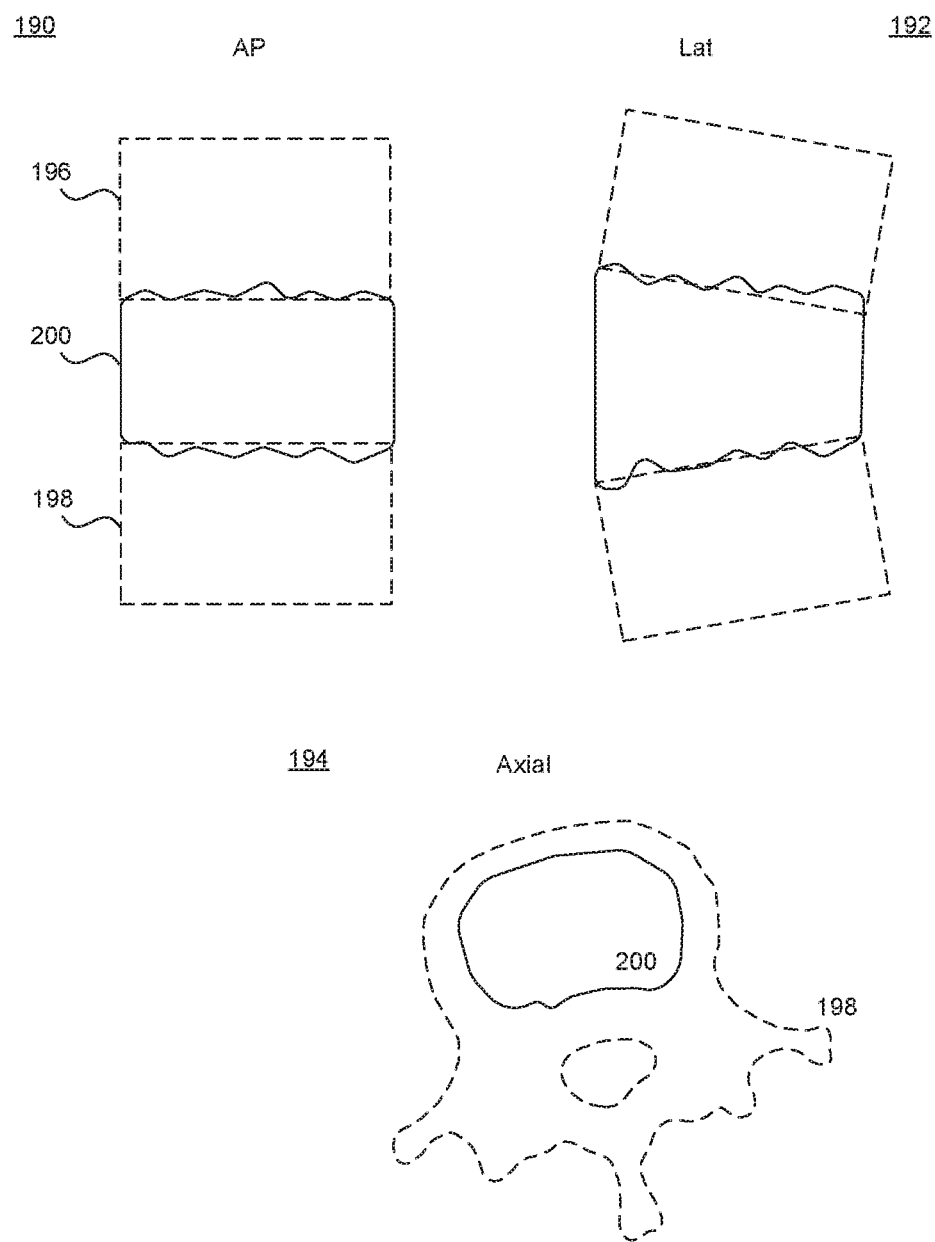
FIG. 12 shows the details of an individual negative space resulting from the adjustment of the relative positions of the vertebrae.

FIG. 12 shows an individual vertebral motion segment comprised of a superior vertebra 196, inferior vertebra 198, and patient-specific interbody (PSIB) implant 200. Three views (AP 190, lateral 192, and axial 194) are shown. PSIB 200 is shown in place with the adjacent vertebrae.

Figure 13:
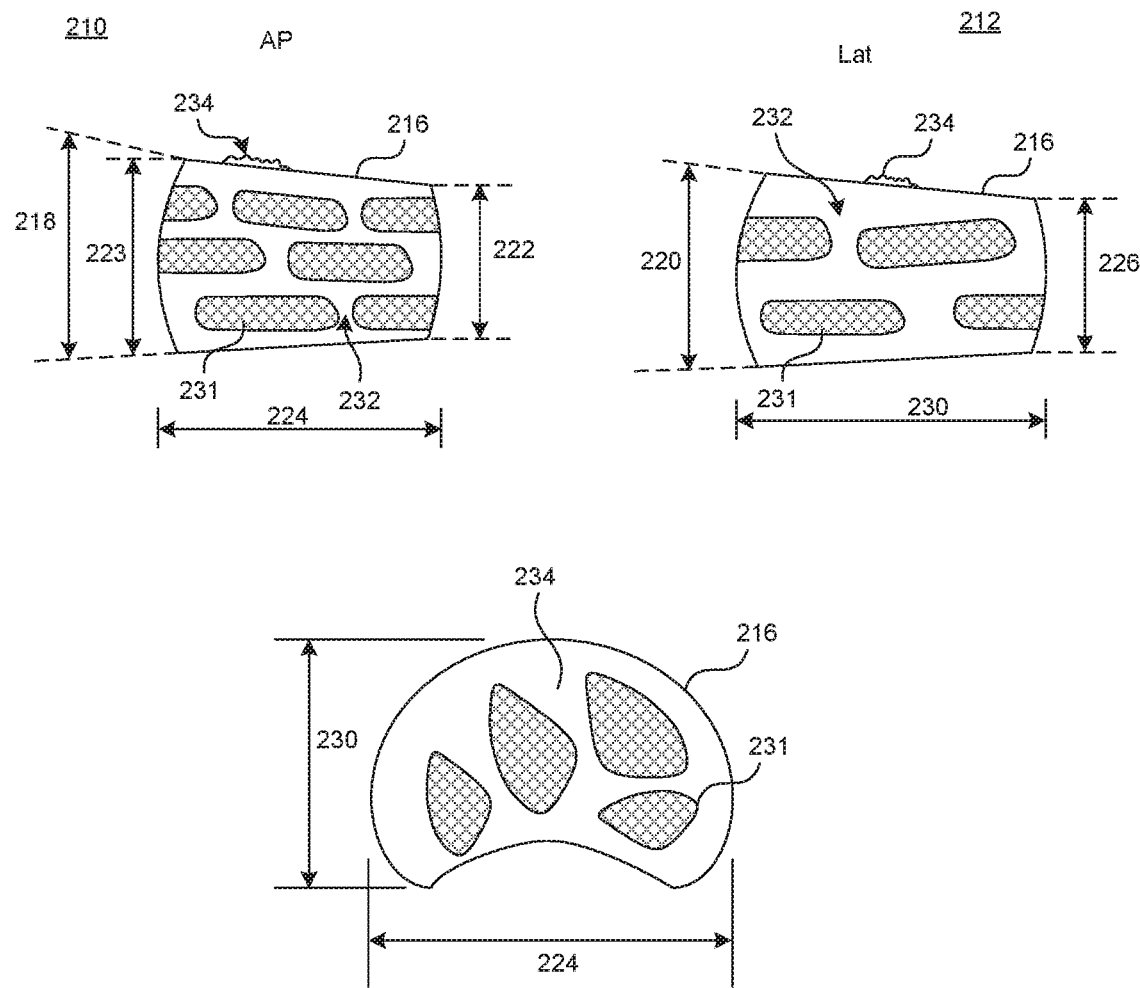
FIG. 13 shows the details of an individual patient-specific implant designed to fill at least a portion of the negative space including bi-planar angulation and endplate topography.

FIG. 13 shows the patient-specific interbody (PSIB) implant 216 displayed in AP 210, lateral 212, and axial 214 views. The PSIB 216 is generated from the three-dimensional negative space created by manipulation of the virtual vertebra into an aligned position.

In each view, several dimensions are shown including, coronal angle 218, sagittal angle 220, left lateral height 222, right lateral height 223, width 224, posterior height 226, and anterior-posterior depth 230. Structural elements or struts 232 can been seen in the AP and lateral views 210, 212. Additionally, internal lattice 231 is shown. Lattice 231 can be designed to resist compressive loads and reduce incidences of subsidence in patients with reduced bone density, including those with osteoporosis.

Another feature of PSIB 216 is endplate topography 234. The endplate of the implant can be designed to match the irregular surface of the adjacent vertebral endplate. The topography can have macro- or micro-geometry to encourage fit, fixation, and fusion to the adjacent vertebral endplate.

In another embodiment, surfaces of the patient-specific interbody implant can be configured to encourage bone growth. It has been shown in clinical literature that structures having a particular pore size can encourage attachment of cells that become a precursor for bone formation. One embodiment can be configured to have the appropriate pore size to encourage bone formation.

Additionally, surfaces of the implant can be impregnated with therapeutic agents including anti-inflammatory compounds, antibiotics, or bone proteins. The impregnation could occur as a result of exposing the implant to solution containing the therapeutic agents, manufacturing therapeutic agents into the substrate or surface material, coating the implant with a therapeutic solution, among other methods. In one embodiment, the therapeutic agents can be configured for a timed release to optimize effectiveness.

Figure 14:
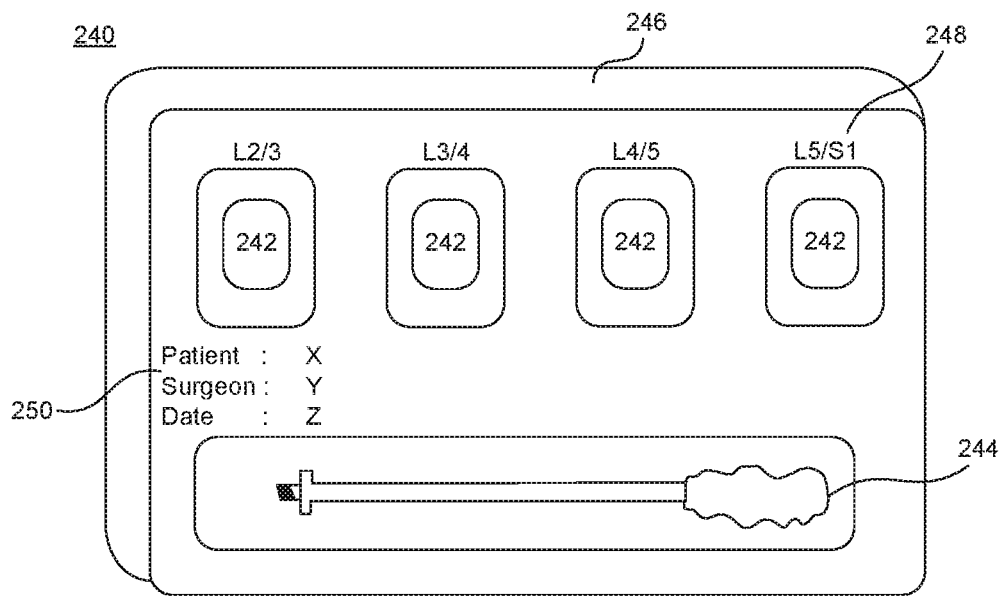
FIG. 14 shows the contents of one embodiment of a patient-specific surgical implant kit, including implants and implant inserter.

FIG. 14 shows a surgical kit 240 including implants 242, instrument 244, and packaging 246. Surgical kit 240 can be assembled and delivered sterile to the operating room. In one embodiment, patient-specific interbodies 242 can be arranged in individual wells with identifiers 248 including level to implanted, external dimensions, and implant strength. Additional data 250 including patient identifier, surgeon identifier, and surgery date can be included in the data. Display of translation, rotation, manipulations to inform surgeon of amount and direction of correction expected in order to reach optimal alignment.

Figure 17:
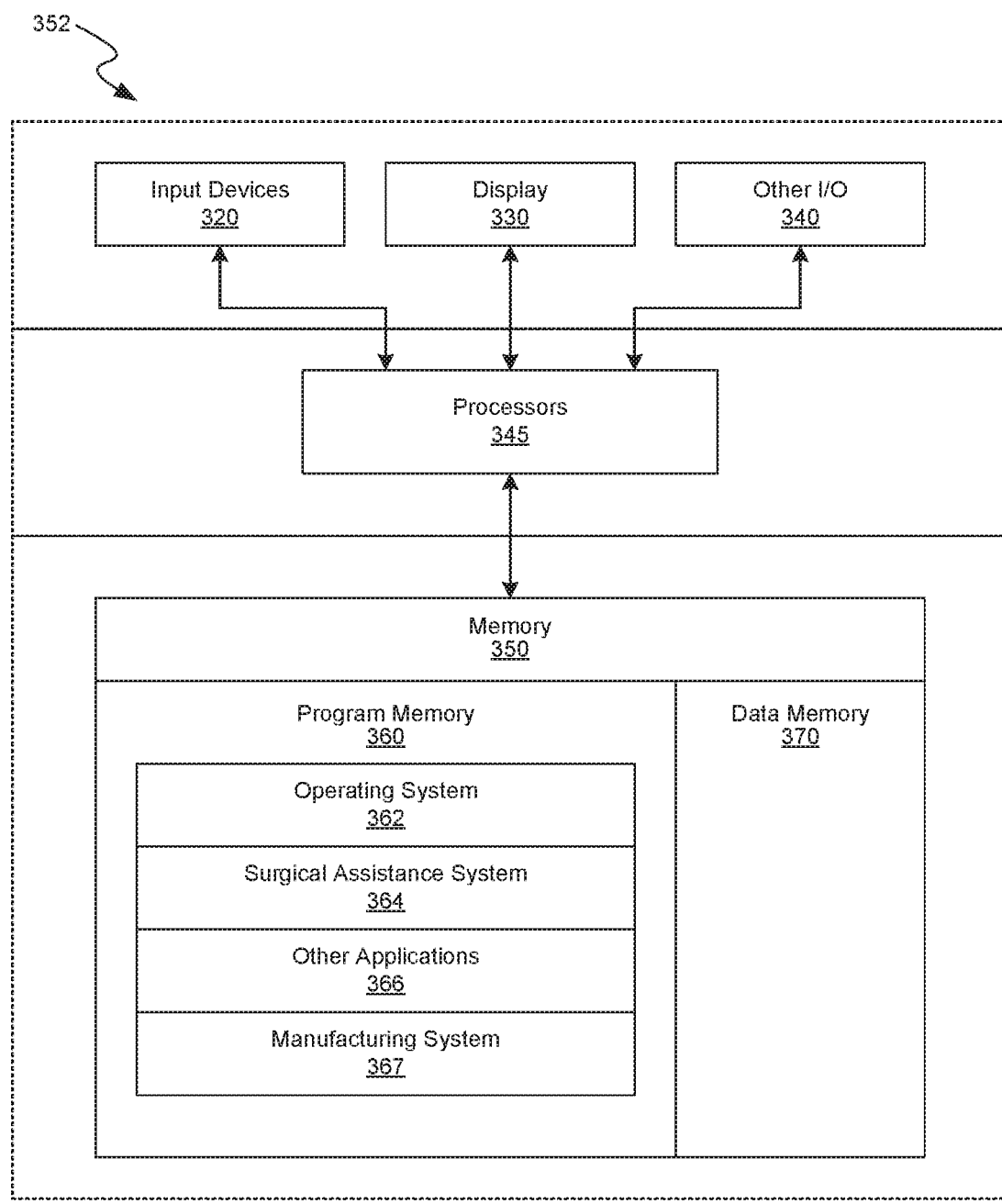
FIG. 17 illustrates a system for providing assistance for manufacturing a patient specific-implant.

FIG. 17 illustrates a system 352 for providing assistance for manufacturing a patient specific-implant. The system 352 can include a surgical assistance system 364 that obtains implant surgery information (e.g., digital data, images of anatomy, correction procedure data, etc.), convert the implant surgery information into a form compatible with an analysis procedure, apply the analysis procedure to obtain results, and use the results to manufacture the patient-specific implant. In some embodiments, the system 352 segments an image of anatomy and then isolates anatomic elements in the image. Spatial relationships between the isolated anatomic elements can be manipulated and negative spaces between anatomic elements can be analyzed or mapped for configuring a virtual implant. In some embodiments, the system 352 can analyze one or more images of the subject to determine an virtual implant configuration, which can include characteristics, such as parameters (e.g., dimensions), materials, angles, application features (e.g., implant sizes, implant functionality, implant placement location, graft chamber sizes, etc.), and/or aspects of applying the implant such as insertion point, delivery path, implant position/angle, rotation, amounts of force to apply, etc.

A patient-specific implant can be manufactured based, at least in part, on the virtual implant configuration selected for the patient. Each patient can receive an implant that is specifically designed for their anatomy. In some procedures, the system 352 can handle the entire design and manufacturing process. In other embodiments, a physician can alter the implant configuration for further customization. An iterative design process can be employed in which the physician and system 352 work together. For example, the system 352 can generate a proposed patient-specific implant. The physician can identify characteristics of the implant to be changed and can input potential design changes. The system 352 can analyze the feedback from the physician to determine a refined patient-specific implant design and to produce a patient-specific model. This process can be repeated any number of times until arriving at a suitable design. Once approved, the implant can be manufactured based on the selected design.

The system 352 can include a surgical assistance system 364 that analyzes implant surgery information, for example, into arrays of integers or histograms, segments images of anatomy, manipulates relationships between anatomic elements, converts patient information into feature vectors, or extracts values from the pre-operative plan. The system 352 can store implant surgery information analyzed by the surgical assistance system 364. The stored information can include received images of a target area, such as MRI scans of a spine, digital images, X-rays, patient information (e.g., sex, weight, etc.), virtual models of the target area, a databased of technology models (e.g., CAD models), and/or a surgeon's pre-operative plan.

In some implementations, surgical assistance system 364 can analyze patient data to identify or develop a corrective procedure, identify anatomical features, etc. The anatomical features can include, without limitation, vertebra, vertebral discs, bony structures, or the like. The surgical assistance system 364 can determine the implant configuration based upon, for example, a corrective virtual model of the subject's spine, risk factors, surgical information (e.g., delivery paths, delivery instruments, etc.), or combinations thereof. In some implementations, the physician can provide the risk factors before or during the procedure. Patient information can include, without limitation, patient sex, age, bone density, health rating, or the like.

In some implementations, the surgical assistance system 364 can apply analysis procedures by supplying implant surgery information to a machine learning model trained to select implant configurations. For example, a neural network model can be trained to select implant configurations for a spinal surgery. The neural network can be trained with training items each comprising a set of images (e.g., camera images, still images, scans, MRI scans, CT scans, X-ray images, laser-scans, etc.) and patient information, an implant configuration used in the surgery, and/or a scored surgery outcome resulting from one or more of: surgeon feedback, patient recovery level, recovery time, results after a set number of years, etc. This neural network can receive the converted surgery information and provide output indicating the pedicle screw configuration.

The assistance system 364 can generate one or more virtual models (e.g., 2D models, 3D models, CAD models, etc.) for designing and manufacturing items. For example, the surgical assistance system 364 can build a virtual model of a surgery target area suitable for manufacturing surgical items, including implants. The surgical assistance system 364 can also generate implant manufacturing information, or data for generating manufacturing information, based on the computed implant configuration. The models can represent the patient's anatomy, implants, candidate implants, etc. The model can be used to (1) evaluate locations (e.g., map a negative 2D or 3D space), (2) select a bounding anatomical feature, such as a vertebral endplate, (3) create a best-fit virtual implant, (4) define a perimeter of the anatomical feature, and/or (5) extrude a volume defined by the perimeter and perpendicular to, for example, a best-fit plane to the interface of another anatomical feature. Anatomical features in the model can be manipulated according to a corrective procedure. Implants, instruments, and surgical plans can be developed based on the pre or post-manipulated model. Neural networks can be trained to generate and/or modify models, as well as other data, including manufacturing information (e.g., data, algorithms, etc.).

In another example, the surgical assistance system 364 can apply the analysis procedure by performing a finite element analysis on a generated three-dimensional model to assess, for example, stresses, strains, deformation characteristics (e.g., load deformation characteristics), fracture characteristics (e.g., fracture toughness), fatigue life, etc. The surgical assistance system 364 can generate a three-dimensional mesh to analyze the model. Machine learning techniques to create an optimized mesh based on a dataset of vertebrae, bones, implants, tissue sites, or other devices. After performing the analysis, the results could be used to refine the selection of implants, implant components, implant type, implantation site, etc.

The surgical assistance system 364 can perform a finite element analysis on a generated three-dimensional model (e.g., models of the spine, vertebrae, implants, etc.) to assess stresses, strains, deformation characteristics (e.g., load deformation characteristics), fracture characteristics (e.g., fracture toughness), fatigue life, etc. The surgical assistance system 364 can generate a three-dimensional mesh to analyze the model of the implant. Based on these results, the configuration of the implant can be varied based on one or more design criteria (e.g., maximum allowable stresses, fatigue life, etc.). Multiple models can be produced and analyzed to compare different types of implants, which can aid in the selection of a particular implant configuration.

The surgical assistance system 364 can incorporate results from the analysis procedure in suggestions. For example, the results can be used to suggest a surgical plan (e.g., a PLIF plan, a TLIF plan, a LLIF plan, a ALIF plan, etc.), select and configure an implant for a procedure, annotate an image with suggested insertions points and angles, generate a virtual reality or augmented reality representation (including the suggested implant configurations), provide warnings or other feedback to surgeons during a procedure, automatically order the necessary implants, generate surgical technique information (e.g., insertion forces/torques, imaging techniques, delivery instrument information, or the like), etc. The suggestions can be specific to implants. In some procedures, the surgical assistance system 364 can also be configured to provide suggestions for conventional implants. In other procedures, the surgical assistance system 364 can be programmed to provide suggestions for patient-specific or customized implants. The suggestion for the conventional implants may be significantly different from suggestions for patient-specific or customized implants.

The system 352 can simulate procedures using a virtual reality system or modeling system. One or more design parameters (e.g., dimensions, implant configuration, instrument, guides, etc.) can be adjusted based, at least in part, on the simulation. Further simulations (e.g., simulations of different corrective procedures) can be performed for further refining implants. In some embodiments, design changes are made interactively with the simulation and the simulated behavior of the device based on those changes. The design changes can include material properties, dimensions, or the like.

The surgical assistance system 364 can improve efficiency, precision, and/or efficacy of implant surgeries by providing more optimal implant configuration, surgical guidance, customized surgical kits (e.g., on-demand kits), etc. This can reduce operational risks and costs produced by surgical complications, reduce the resources required for preoperative planning efforts, and reduce the need for extensive implant variety to be prepared prior to an implant surgery. The surgical assistance system 364 provides increased precision and efficiency for patients and surgeons.

In orthopedic surgeries, the surgical assistance system 364 can select or recommend implants, surgical techniques, patient treatment plans, or the like. In spinal surgeries, the surgical assistance system 364 can select interbody implants, pedicle screws, and/or surgical techniques to make surgeons more efficient and precise, as compared to existing surgical kits and procedures. The surgical assistance system 364 can also improve surgical robotics/navigation systems, and provide improved intelligence for selecting implant application parameters. For example, the surgical assistance system 364 empowers surgical robots and navigation systems for spinal surgeries to increase procedure efficiency and reduce surgery duration by providing information on types and sizes, along with expected insertion angles. In addition, hospitals benefit from reduced surgery durations and reduced costs of purchasing, shipping, and storing alternative implant options. Medical imaging and viewing technologies can integrate with the surgical assistance system 364, thereby providing more intelligent and intuitive results.

The surgical assistance system 364 can include one or more input devices 420 that provide input to the processor(s) 345 (e.g., CPU(s), GPU(s), HPU(s), etc.), notifying it of actions. The input devices 320 can be used to manipulate a model of the spine, as discussed in connection with FIGS. 10 and 11. The actions can be mediated by a hardware controller that interprets the signals received from the input device and communicates the information to the processors 345 using a communication protocol. Input devices 320 include, for example, a mouse, a keyboard, a touchscreen, an infrared sensor, a touchpad, a wearable input device, a camera- or image-based input device, a microphone, or other user input devices. Processors 345 can be a single processing unit or multiple processing units in a device or distributed across multiple devices. Processors 345 can be coupled to other hardware devices, for example, with the use of a bus, such as a PCI bus or SCSI bus.

The system 352 can include a display 300 used to display text, models, virtual procedures, surgical plans, implants, and graphics. In some implementations, display 330 provides graphical and textual visual feedback to a user. In some implementations, display 330 includes the input device as part of the display, such as when the input device is a touchscreen or is equipped with an eye direction monitoring system. The processors 345 can communicate with a hardware controller for devices, such as for a display 330. In some implementations, the display is separate from the input device. Examples of display devices are: an LCD display screen, an LED display screen, a projected, holographic, or augmented reality display (such as a heads-up display device or a head-mounted device), and so on. Other I/O devices 340 can also be coupled to the processors 345, such as a network card, video card, audio card, USB, firewire or other external device, camera, printer, speakers, CD-ROM drive, DVD drive, disk drive, or Blu-Ray device. Other I/O 340 can also include input ports for information from directly connected medical equipment such as imaging apparatuses, including MRI machines, X-Ray machines, CT machines, etc. Other I/O 340 can further include input ports for receiving data from these types of machine from other sources, such as across a network or from previously captured data, for example, stored in a database.

In some implementations, the system 352 also includes a communication device capable of communicating wirelessly or wire-based with a network node. The communication device can communicate with another device or a server through a network using, for example, TCP/IP protocols. System 452 can utilize the communication device to distribute operations across multiple network devices, including imaging equipment, manufacturing equipment, etc.

The system 452 can include memory 350. The processors 345 can have access to the memory 350, which can be in a device or distributed across multiple devices. Memory 350 includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. Memory 350 can include program memory 360 that stores programs and software, such as an operating system 362, surgical assistance system 364, and other application programs 366. Memory 350 can also include data memory 370 that can include, e.g., implant information, configuration data, settings, user options or preferences, etc., which can be provided to the program memory 360 or any element of the system 352, such as the manufacturing system 367. The system 452 can be programmed to perform the methods discussed in connection with FIGS. 18 and 19 to manufacture implants using the manufacturing system 367.

Figure 18:
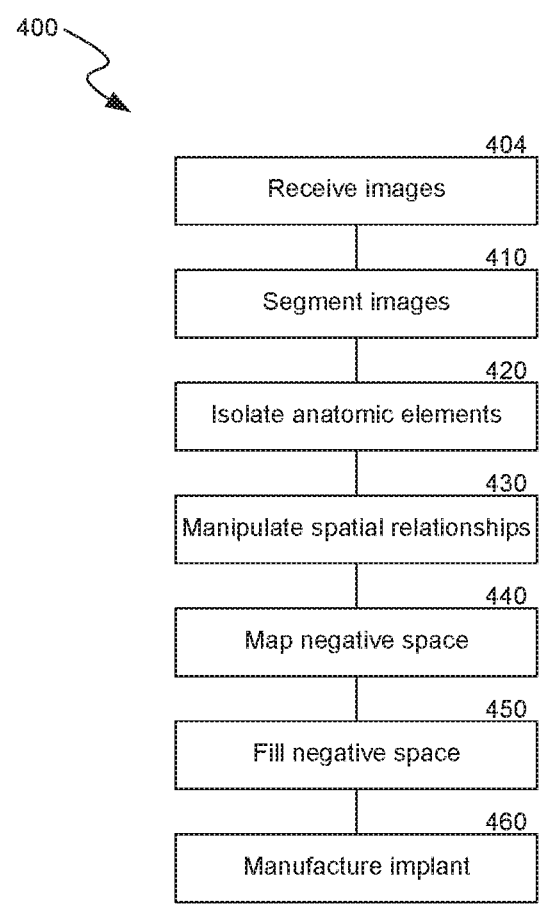
FIG. 18 is a flow diagram illustrating a method for manufacturing an implant in accordance with an embodiment.

FIG. 18 is a flow diagram illustrating a method 400 for manufacturing an implant in accordance with an embodiment of the disclosure. At block 404, one or more images of anatomy are received. At block 410, features in images can be segmented. The features can be anatomy of interest, such as bone, organs, etc. Anatomic elements (e.g., vertebrae, vertebral disks, etc.) can be isolated at block 420. At block 430, spatial relationships between the isolated anatomic elements can be manipulated. Before and/or after manipulating the spatial relationships, a negative space between anatomic elements can be mapped at block 440. At block 450, at least a portion of the negative space can be filled with a virtual implant. At block 460, the virtual implant can be used to select, design, and/or manufacture a patient-specific implant (e.g., implant 110 of FIG. 6).

Figure 19:
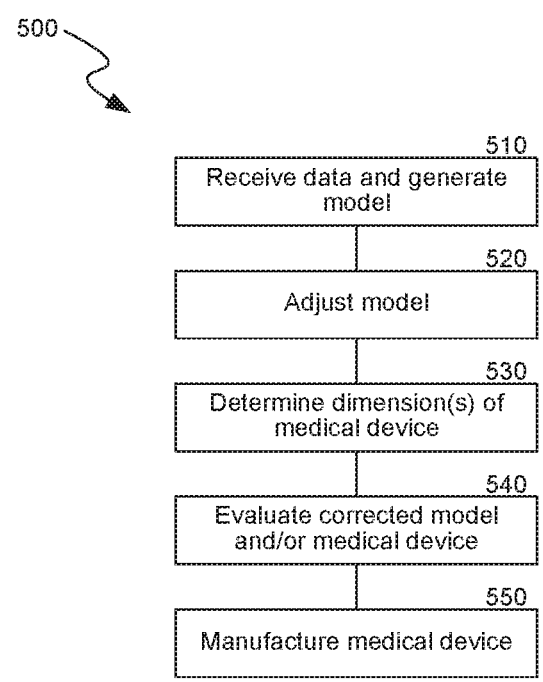
FIG. 19 is a flow diagram illustrating a method for manufacturing an implant in accordance with another embodiment.

FIG. 19 is a flow diagram illustrating a method 500 for manufacturing an implant in accordance with an embodiment of the disclosure. At block 510, a system can receive patient data and generate a patient-specific model based on the received patient data. At block 520, the patient-specific model can be adjusted according to one or more corrective procedures to produce a corrected model. The corrected model can be used to design a patient specific medical device. In some embodiments, the corrected model can be a 2D or 3D anatomical model of the patient's spine, vertebral column, etc. At block 530, dimensions of a virtual implant/medical device can be determined using the corrected model. For example, the size of the virtual implant/medical device can be determined by positioning a virtual implant/medical device at a desired location (e.g., an implantation site in the corrected model). At block 540, once positioned, the corrected anatomical model and/or virtual implant can be evaluated to assess expected treatment outcomes, performance of the virtual implant (e.g., fatigue life, loading characteristics, etc.), or the like. For example, contact and load transfer can be analyzed. The corrected model can be adjusted to properly position anatomic elements with respect to the virtual implant/medical device.

The patient data can include images of the patient's body, clinician input, treatment plan information, or the like. The corrected model can be generated by processing (e.g., segmenting, filtering, edge detection, partitioning, etc.) the images and then analyzing, for example, anatomical features of interest. Anatomical features can be manipulated (e.g., resized, moved, translated, rotated, etc.) to generate the corrected model. The corrected model can be used to simulate different procedures with different virtual implants. At block 550, patient-specific implants (e.g., implant 110 of FIG. 6) can be produced based on the virtual implants, models, simulations, etc.

The methods (e.g., methods 400 and 500) can include other steps disclosed herein. Some implementations can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

The embodiments, features, systems, devices, materials, methods and techniques described herein may, in some embodiments, be similar to any one or more of the embodiments, features, systems, devices, materials, methods and techniques described in the following:

U.S. application Ser. No. 16/048,167, filed on Jul. 27, 2017, titled "SYSTEMS AND METHODS FOR ASSISTING AND AUGMENTING SURGICAL PROCEDURES;"

U.S. application Ser. No. 16/242,877, filed on Jan. 8, 2019, titled "SYSTEMS AND METHODS OF ASSISTING A SURGEON WITH SCREW PLACEMENT DURING SPINAL SURGERY;"

U.S. application Ser. No. 16/207,116, filed on Dec. 1, 2018, titled "SYSTEMS AND METHODS FOR MULTI-PLANAR ORTHOPEDIC ALIGNMENT;"

U.S. application Ser. No. 16/383,215, filed on Apr. 12, 2019, titled "SYSTEMS AND METHODS FOR ORTHOPEDIC IMPLANT FIXATION;" and U.S. Application No. 62/773,127, filed on Nov. 29, 2018, titled "SYSTEMS AND METHODS FOR ORTHOPEDIC IMPLANTS."

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

While embodiments have been shown and described, various modifications may be made without departing from the scope of the inventive concepts disclosed herein.

What is claimed is:

1. A computer-implemented method for manufacturing an orthopedic implant, comprising:
   segmenting anatomy of interest in at least one image of a subject;
   isolating separate anatomic elements of the anatomy of interest;
   manipulating spatial relationships between the isolated anatomic elements; and
   after manipulating the spatial relationships,
      mapping a negative space between the anatomic elements, and filling at least a portion of the negative space with a virtual implant.

2. The method of claim 1, further comprising after manipulating the spatial relationships,
generating one or more parameters of the virtual implant based on relative positions of the anatomic elements.

3. The method of claim 1, wherein manipulating the spatial relationships includes positioning the isolated anatomic elements at positions corresponding to a corrective procedure.

4. The method of claim 1, further comprising manufacturing the orthopedic implant according to one or more parameters of the virtual implant determined based on filling the at least the portion of the negative space with the virtual implant.

5. The method of claim 1, wherein the at least one image includes a CT scan, an MRI scan, and/or an X-ray.

6. The method of claim 1, further comprising imaging the anatomy of interest.

7. The method of claim 6, wherein the imaging step is accomplished by using a CT machine, an MRI machine, and/or orthogonal bi-planar x-ray.

8. The method of claim 1, wherein the segmenting step is accomplished by using a threshold filter and/or a combination of filters.

9. The method of claim 1, wherein the isolating step is accomplished by using a volumetric grow operation.

10. The method of claim 1, wherein the manipulating step is accomplished by translating the isolated body along an axis.

11. The method of claim 1, wherein the manipulating step is accomplished by rotating the isolated element about an axis.

12. The method of claim 1, wherein the manipulating step is accomplished by translating the isolated element about a curve.

13. The method of claim 1, wherein the mapping step is accomplished by selecting a first bounding anatomical feature, selecting at least a second bounding anatomical feature and calculating the volume between the first and second bounding anatomical features.

14. The method of claim 1 further comprising defining an implant boundary.

15. The method of claim 4, wherein the manufacturing step is accomplished by 3D printing, additive manufacturing, and/or subtractive manufacturing.

16. The method of claim 1, further comprising manufacturing an implant with surfaces configured for timely release of therapeutic elements including antibiotics, anti-inflammatory, and/or bone proteins.

17. The method of claim 1, further comprising:
creating a 3D model of the virtual implant based on the filling of the negative space with the virtual implant;
converting the 3D model into 3D fabrication data; and
manufacturing at least a portion of the orthopedic implant based on the 3D fabrication data.

18. The method of claim 1, further comprising generating a virtual three-dimensional model of the anatomy of interest with the negative space.

19. The method of claim 18, wherein filling the at least the portion of the negative space with the virtual implant is performed using the negative space of the virtual three-dimensional model.

20. The method of claim 1, wherein the negative space is a three-dimensional negative space between the anatomic elements represented by virtual three-dimensional anatomic elements.

21. The method of claim 1, wherein manipulating the spatial relationships between the isolated anatomic elements includes moving the anatomic elements to provide a corrective virtual model of the subject's spine with the negative space.

22. The method of claim 1, further comprising generating a virtual three-dimensional corrective model of the subject's spine with the negative space.

23. The method of claim 22, wherein filling the at least the portion of the negative space with the virtual implant is performed using the negative space of the virtual three-dimensional corrective model, wherein the virtual implant is a spine implant.

24. The method of claim 22, wherein the negative space is a three-dimensional negative space between the anatomic elements represented by virtual three-dimensional anatomic elements.

25. A method for creating an orthopedic implant, the method comprising:
imaging anatomy;
segmenting anatomy of interest;
isolating separate anatomic elements;
manipulating spatial relationships between anatomic elements;
identifying a negative space between anatomic elements;
filling at least a portion of the negative space with a virtual implant; and
manufacturing an implant from one or more parameters of the virtual implant.

26. The method of claim 25, wherein the identifying step is accomplished by selecting a first bounding anatomical feature, selecting at least a second bounding anatomical feature and calculating the volume between bounding anatomical features.

27. The method of claim 25, further comprising generating a virtual three-dimensional corrective model of the anatomy of interest, wherein the virtual three-dimensional corrective model defines the negative space.

28. The method of claim 27, wherein filling the at least the portion of the negative space with the virtual implant is performed using the negative space of the virtual three-dimensional corrective model.

29. The method of claim 25, wherein the negative space is a three-dimensional negative space between the anatomic elements represented by virtual three-dimensional anatomic elements in a corrected configuration.

30. The method of claim 25, wherein manipulating the spatial relationships between anatomic elements includes moving the anatomic elements to provide a corrective virtual model.

* * * * *